United States Patent
Lion et al.

(10) Patent No.: US 7,932,324 B2
(45) Date of Patent: Apr. 26, 2011

(54) BLOCK POLYMERS AND COSMETIC COMPOSITIONS AND PROCESSES COMPRISING THEM

(75) Inventors: Bertrand Lion, Luzarches (FR); Nathalie Martin, Viarnes (FR); Béatrice Toumi, Verrieres le Buisson (FR)

(73) Assignee: L'Oreal, Paris (FR)

( * ) Notice: Subject to any disclaimer, the term of this patent is extended or adjusted under 35 U.S.C. 154(b) by 704 days.

(21) Appl. No.: 11/859,015

(22) Filed: Sep. 21, 2007

(65) Prior Publication Data

US 2008/0014235 A1 Jan. 17, 2008

Related U.S. Application Data

(62) Division of application No. 10/670,478, filed on Sep. 26, 2003, now Pat. No. 7,803,877.

(30) Foreign Application Priority Data

Sep. 26, 2002 (FR) .................................... 02 11949
May 21, 2003 (FR) .................................... 03 06121

(51) Int. Cl.
*C08F 293/00* (2006.01)
(52) U.S. Cl. .................. 525/299; 424/78.02; 424/78.31; 424/401; 424/407
(58) Field of Classification Search .............. 424/78.02, 424/78.31, 401, 407; 525/299
See application file for complete search history.

(56) References Cited

U.S. PATENT DOCUMENTS

| | | | |
|---|---|---|---|
| 2,047,398 A | 7/1936 | Voss et al. | |
| 2,528,378 A | 10/1950 | Mannheimer et al. | |
| 2,723,248 A | 11/1955 | Wright | |
| 2,781,354 A | 2/1957 | Mannheimer et al. | |
| 3,673,160 A | 6/1972 | Buisson et al. | |
| 3,716,633 A | 2/1973 | Viout et al. | |
| 3,802,841 A | 4/1974 | Robin | |
| 3,836,537 A | 9/1974 | Boerwinkle et al. | |
| 3,910,862 A | 10/1975 | Barabas et al. | |
| 3,915,921 A | 10/1975 | Schlatzer et al. | |
| 3,925,542 A | 12/1975 | Viout et al. | |
| 3,937,811 A | 2/1976 | Papantoniou et al. | |
| 3,946,749 A | 3/1976 | Papantoniou | |
| 3,966,403 A | 6/1976 | Papantoniou et al. | |
| 3,966,404 A | 6/1976 | Papantoniou et al. | |
| 3,990,459 A | 11/1976 | Papantoniou | |
| 4,030,512 A | 6/1977 | Papantoniou et al. | |
| 4,031,307 A | 6/1977 | DeMartino et al. | |
| 4,032,628 A | 6/1977 | Papantoniou et al. | |
| 4,070,533 A | 1/1978 | Papantoniou et al. | |
| 4,076,912 A | 2/1978 | Papantoniou et al. | |
| RE29,871 E | 12/1978 | Papantoniou et al. | |
| 4,128,631 A | 12/1978 | Lundmark et al. | |
| 4,129,711 A | 12/1978 | Viout et al. | |
| 4,131,576 A | 12/1978 | Iovine | |
| 4,137,208 A | 1/1979 | Elliott | |
| 4,152,416 A | 5/1979 | Spitzer et al. | |
| 4,165,367 A | 8/1979 | Chakrabarti | |
| 4,223,009 A | 9/1980 | Chakrabarti | |
| 4,282,203 A | 8/1981 | Jacquet et al. | |
| 4,289,752 A | 9/1981 | Mahieu et al. | |
| 4,425,326 A | 1/1984 | Guillon et al. | |
| 4,509,949 A | 4/1985 | Huang et al. | |
| 4,693,935 A | 9/1987 | Mazurek | |
| 4,728,571 A | 3/1988 | Clemens et al. | |
| 4,887,622 A | 12/1989 | Gueret | |
| 4,972,037 A | 11/1990 | Garbe et al. | |
| 4,981,902 A | 1/1991 | Mitra et al. | |
| 4,981,903 A | 1/1991 | Garbe et al. | |
| 5,000,937 A | 3/1991 | Grollier et al. | |
| 5,061,481 A | 10/1991 | Suzuki et al. | |
| 5,110,582 A | 5/1992 | Hungerbuhler et al. | |
| 5,156,911 A | 10/1992 | Stewart | |
| 5,209,924 A | 5/1993 | Garbe et al. | |
| 5,219,560 A | 6/1993 | Suzuki et al. | |
| 5,266,321 A | 11/1993 | Shukuzaki | |
| 5,362,485 A | 11/1994 | Hayama et al. | |
| 5,391,631 A | 2/1995 | Porsch et al. | |
| 5,468,477 A | 11/1995 | Kumar et al. | |
| 5,472,798 A | 12/1995 | Kumazawa et al. | |
| 5,492,426 A | 2/1996 | Gueret | |
| 5,519,063 A | 5/1996 | Mondet et al. | |
| 5,538,717 A | 7/1996 | La Poterie | |
| 5,681,877 A | 10/1997 | Hosotte-Filbert et al. | |
| 5,686,067 A | 11/1997 | Shih et al. | |
| 5,690,918 A | 11/1997 | Jacks et al. | |

(Continued)

FOREIGN PATENT DOCUMENTS

DE 2 330 956 1/1974

(Continued)

OTHER PUBLICATIONS

English language Abstract of FR 2 710 552.
English language Abstract of FR 2 710 646.
English language Abstract of FR 2 791 987.
English language Abstract of FR 2 832 719.
English language Abstract of FR 2 832 720.
English language Abstract of JP H07-309721.
English language Abstract of JP H08-119836.
English language Abstract of JP H11-100307.
English language Abstract of WO 01/13863.
English language Abstract of WO 01/51018.

(Continued)

*Primary Examiner* — Bernard Lipman
(74) *Attorney, Agent, or Firm* — Finnegan, Henderson, Farabow, Garrett & Dunner LLP

(57) ABSTRACT

The present invention relates to novel block polymers comprising at least one first block and at least one second block that are incompatible with each other, have different glass transition temperatures (Tg), and are linked together via an intermediate segment comprising at least one constituent monomer of the at least one first block and at least one constituent monomer of the at least one second block. The block polymer has a polydispersity index I of greater than 2. The invention also relates to cosmetic compositions comprising the block polymers and processes for their use.

32 Claims, No Drawings

U.S. PATENT DOCUMENTS

| | | |
|---|---|---|
| 5,711,940 A | 1/1998 | Kuentz et al. |
| 5,725,882 A | 3/1998 | Kumar et al. |
| 5,736,125 A | 4/1998 | Morawsky et al. |
| 5,747,013 A | 5/1998 | Mougin et al. |
| 5,756,635 A | 5/1998 | Michaud et al. |
| 5,772,347 A | 6/1998 | Gueret |
| 5,783,657 A | 7/1998 | Pavlin et al. |
| 5,807,540 A | 9/1998 | Junino et al. |
| 5,849,275 A | 12/1998 | Calello et al. |
| 5,849,318 A | 12/1998 | Imai et al. |
| 5,879,095 A | 3/1999 | Gueret |
| 5,897,870 A | 4/1999 | Schehlmann et al. |
| 5,948,393 A | 9/1999 | Tomomasa et al. |
| 5,994,446 A | 11/1999 | Graulus et al. |
| 6,001,367 A | 12/1999 | Bazin et al. |
| 6,001,374 A | 12/1999 | Nichols |
| 6,027,739 A | 2/2000 | Nichols |
| 6,033,650 A | 3/2000 | Calello et al. |
| 6,059,473 A | 5/2000 | Gueret |
| 6,074,654 A | 6/2000 | Drechsler et al. |
| 6,083,516 A | 7/2000 | Curtis et al. |
| 6,106,813 A | 8/2000 | Mondet et al. |
| 6,106,820 A | 8/2000 | Morrissey et al. |
| 6,120,781 A | 9/2000 | Le Bras et al. |
| 6,126,929 A | 10/2000 | Mougin |
| 6,132,742 A | 10/2000 | Le Bras et al. |
| 6,139,849 A | 10/2000 | Lesaulnier et al. |
| 6,140,431 A | 10/2000 | Kinker et al. |
| 6,153,206 A | 11/2000 | Anton et al. |
| 6,156,804 A | 12/2000 | Chevalier et al. |
| 6,160,054 A | 12/2000 | Schwindeman et al. |
| 6,165,457 A | 12/2000 | Midha et al. |
| 6,166,093 A | 12/2000 | Mougin et al. |
| 6,174,968 B1 | 1/2001 | Hoxmeier |
| 6,180,123 B1 | 1/2001 | Mondet |
| 6,197,883 B1 | 3/2001 | Schimmel et al. |
| 6,225,390 B1 | 5/2001 | Hoxmeier |
| 6,228,946 B1 | 5/2001 | Kitayama et al. |
| 6,228,967 B1 | 5/2001 | Fost et al. |
| 6,238,679 B1 | 5/2001 | De La Poterie |
| 6,254,878 B1 | 7/2001 | Bednarek et al. |
| 6,258,916 B1 | 7/2001 | Michaud et al. |
| 6,267,951 B1 | 7/2001 | Shah et al. |
| 6,268,466 B1 | 7/2001 | MacQueen et al. |
| 6,280,713 B1 | 8/2001 | Tranchant et al. |
| 6,303,105 B1 | 10/2001 | Shah et al. |
| 6,319,959 B1 | 11/2001 | Mougin et al. |
| 6,326,011 B1 | 12/2001 | Miyazawa et al. |
| 6,328,495 B1 | 12/2001 | Gueret |
| 6,342,237 B1 | 1/2002 | Bara |
| 6,372,876 B1 | 4/2002 | Kim et al. |
| 6,386,781 B1 | 5/2002 | Gueret |
| 6,395,265 B1 | 5/2002 | Mougin et al. |
| 6,399,691 B1 | 6/2002 | Melchiors et al. |
| 6,410,005 B1 | 6/2002 | Galleguillos et al. |
| 6,410,666 B1 | 6/2002 | Grubbs et al. |
| 6,412,496 B1 | 7/2002 | Gueret |
| 6,423,306 B2 | 7/2002 | Caes et al. |
| 6,464,969 B2 | 10/2002 | De La Poterie et al. |
| 6,484,731 B1 | 11/2002 | Lacout |
| 6,491,927 B1 | 12/2002 | Arnaud et al. |
| 6,518,364 B2 | 2/2003 | Charmot et al. |
| 6,531,535 B2 | 3/2003 | Melchiors et al. |
| 6,552,146 B1 | 4/2003 | Mougin |
| 6,581,610 B1 | 6/2003 | Gueret |
| 6,649,173 B1 | 11/2003 | Arnaud et al. |
| 6,663,855 B2 | 12/2003 | Frechet et al. |
| 6,663,885 B1 | 12/2003 | Hager et al. |
| 6,685,925 B2 | 2/2004 | Frechet et al. |
| 6,692,173 B2 | 2/2004 | Gueret |
| 6,692,733 B1 | 2/2004 | Mougin |
| 6,770,271 B2 | 8/2004 | Mondet et al. |
| 6,805,872 B2 | 10/2004 | Mougin |
| 6,833,419 B2 | 12/2004 | Morschhauser et al. |
| 6,843,611 B2 | 1/2005 | Blondeel et al. |
| 6,866,046 B2 | 3/2005 | Gueret |
| 6,881,780 B2 | 4/2005 | Bryant et al. |
| 6,890,522 B2 | 5/2005 | Frechet et al. |
| 6,891,011 B2 | 5/2005 | Morschhauser et al. |
| 6,905,696 B2 | 6/2005 | Marotta et al. |
| 6,946,518 B2 | 9/2005 | De La Poterie |
| 6,960,339 B1 | 11/2005 | Ferrari |
| 6,964,995 B2 | 11/2005 | Morschhauser et al. |
| 7,022,791 B2 | 4/2006 | Loffler et al. |
| 7,025,973 B2 | 4/2006 | Loffler et al. |
| 7,053,146 B2 | 5/2006 | Morschhauser et al. |
| 7,081,507 B2 | 7/2006 | Morschhauser et al. |
| 7,144,171 B2 | 12/2006 | Blondeel et al. |
| 7,151,137 B2 | 12/2006 | Morschhauser et al. |
| 7,176,170 B2 | 2/2007 | Dubief et al. |
| 7,186,405 B2 | 3/2007 | Loeffler et al. |
| 7,186,774 B2 | 3/2007 | Morschhauser et al. |
| 7,244,421 B2 | 7/2007 | Loffler et al. |
| 7,279,154 B2 | 10/2007 | Loffler et al. |
| 7,297,328 B2 | 11/2007 | Loffler et al. |
| 7,332,155 B2 | 2/2008 | Loffler et al. |
| 7,358,303 B2 | 4/2008 | De La Poterie |
| 7,393,520 B2 | 7/2008 | Loeffler et al. |
| 7,399,478 B2 | 7/2008 | Loffler et al. |
| 2002/0015611 A1 | 2/2002 | Blondeel et al. |
| 2002/0018759 A1 | 2/2002 | Pagano et al. |
| 2002/0020424 A1 | 2/2002 | Gueret |
| 2002/0035237 A1 | 3/2002 | Lawson et al. |
| 2002/0054783 A1 | 5/2002 | Gueret |
| 2002/0055562 A1 | 5/2002 | Butuc |
| 2002/0061319 A1 | 5/2002 | Bernard et al. |
| 2002/0064539 A1 | 5/2002 | Philippe et al. |
| 2002/0076390 A1 | 6/2002 | Kantner et al. |
| 2002/0076425 A1 | 6/2002 | Mondet et al. |
| 2002/0098217 A1 | 7/2002 | Piot et al. |
| 2002/0115780 A1 | 8/2002 | Mougin |
| 2002/0150546 A1 | 10/2002 | Mougin et al. |
| 2002/0151638 A1 | 10/2002 | Melchiors et al. |
| 2002/0159965 A1 | 10/2002 | Frechet et al. |
| 2002/0160026 A1 | 10/2002 | Frechet et al. |
| 2003/0003154 A1 | 1/2003 | De La Poterie |
| 2003/0017124 A1 | 1/2003 | Agostini et al. |
| 2003/0017182 A1 | 1/2003 | Tournilhac |
| 2003/0021815 A9 | 1/2003 | Mondet et al. |
| 2003/0024074 A1 | 2/2003 | Hartman |
| 2003/0039621 A1 | 2/2003 | Arnaud et al. |
| 2003/0059392 A1 | 3/2003 | L'Alloret |
| 2003/0113285 A1 | 6/2003 | Meffert et al. |
| 2003/0124074 A1 | 7/2003 | Mougin et al. |
| 2003/0124079 A1 | 7/2003 | Mougin et al. |
| 2003/0185774 A1 | 10/2003 | Dobbs et al. |
| 2003/0191271 A1 | 10/2003 | Mondet et al. |
| 2004/0009136 A1 | 1/2004 | Dubief et al. |
| 2004/0013625 A1 | 1/2004 | Kanji |
| 2004/0014872 A1 | 1/2004 | Raether |
| 2004/0039101 A1 | 2/2004 | Dubief et al. |
| 2004/0052745 A1 | 3/2004 | Bernard et al. |
| 2004/0052752 A1 | 3/2004 | Samain et al. |
| 2004/0077788 A1 | 4/2004 | Guerra et al. |
| 2004/0091444 A1 | 5/2004 | Loffler et al. |
| 2004/0093676 A1 | 5/2004 | Vidal et al. |
| 2004/0096409 A1 | 5/2004 | Loeffler et al. |
| 2004/0096411 A1 | 5/2004 | Frechet et al. |
| 2004/0097657 A1 | 5/2004 | Morschhauser et al. |
| 2004/0109835 A1 | 6/2004 | Loffler et al. |
| 2004/0109836 A1 | 6/2004 | Loffler et al. |
| 2004/0109838 A1 | 6/2004 | Morschhauser et al. |
| 2004/0115148 A1 | 6/2004 | Loffler et al. |
| 2004/0115149 A1 | 6/2004 | Loffler et al. |
| 2004/0115157 A1 | 6/2004 | Loffler et al. |
| 2004/0116628 A1 | 6/2004 | Morschhauser et al. |
| 2004/0116634 A1 | 6/2004 | Morschhauser et al. |
| 2004/0120906 A1 | 6/2004 | Toumi et al. |
| 2004/0120920 A1 | 6/2004 | Lion et al. |
| 2004/0137020 A1 | 7/2004 | De La Poterie et al. |
| 2004/0137021 A1 | 7/2004 | De La Poterie et al. |
| 2004/0141937 A1 | 7/2004 | Loffler et al. |
| 2004/0141943 A1 | 7/2004 | Mougin et al. |
| 2004/0142831 A1 | 7/2004 | Jager Lezer |
| 2004/0167304 A1 | 8/2004 | Morschhauser et al. |
| 2004/0223933 A1 | 11/2004 | Hiwatashi et al. |
| 2004/0241118 A1 | 12/2004 | Simon et al. |

| | | | | | | |
|---|---|---|---|---|---|---|
| 2005/0002724 | A1 | 1/2005 | Blondeel et al. | EP | 1 518 535 | 3/2005 |
| 2005/0020779 | A1 | 1/2005 | Mougin et al. | EP | 1 604 634 | 12/2005 |
| 2005/0032998 | A1 | 2/2005 | Morschhaeuser et al. | FR | 1 222 944 | 6/1960 |
| 2005/0089536 | A1 | 4/2005 | Loffler et al. | FR | 1 400 366 | 4/1965 |
| 2005/0095213 | A1 | 5/2005 | Blin et al. | FR | 1 564 110 | 3/1969 |
| 2005/0106197 | A1 | 5/2005 | Blin et al. | FR | 1 580 545 | 9/1969 |
| 2005/0129641 | A1 | 6/2005 | Arnaud et al. | FR | 2 077 143 | 9/1971 |
| 2005/0201958 | A1 | 9/2005 | De La Poterie | FR | 2 079 785 | 11/1971 |
| 2005/0220747 | A1 | 10/2005 | Lion et al. | FR | 2 140 977 | 1/1973 |
| 2005/0232887 | A1 | 10/2005 | Morschhauser et al. | FR | 2 232 303 | 1/1975 |
| 2005/0287103 | A1 | 12/2005 | Filippi et al. | FR | 2 265 781 | 10/1975 |
| 2006/0093568 | A1 | 5/2006 | Blin et al. | FR | 2 265 782 | 10/1975 |
| 2006/0099164 | A1 | 5/2006 | De la Poterie et al. | FR | 2 350 384 | 12/1977 |
| 2006/0099231 | A1 | 5/2006 | De La Poterie et al. | FR | 2 357 241 | 2/1978 |
| 2006/0115444 | A1 | 6/2006 | Blin et al. | FR | 2 393 573 | 1/1979 |
| 2006/0127334 | A1 | 6/2006 | Ferrari et al. | FR | 2 439 798 | 5/1980 |
| 2006/0134032 | A1 | 6/2006 | Ilekti et al. | FR | 2 710 552 | 4/1995 |
| 2006/0134038 | A1 | 6/2006 | De La Poterie et al. | FR | 2 710 646 | 4/1995 |
| 2006/0134044 | A1 | 6/2006 | Blin et al. | FR | 2 722 380 | 6/1996 |
| 2006/0134051 | A1 | 6/2006 | Blin et al. | FR | 2 727 609 | 6/1996 |
| 2006/0147402 | A1 | 7/2006 | Blin et al. | FR | 2 743 297 | 7/1997 |
| 2006/0147403 | A1 | 7/2006 | Ferrari et al. | FR | 2 761 959 | 10/1998 |
| 2007/0003506 | A1 | 1/2007 | Mougin et al. | FR | 2 796 529 | 7/1999 |
| 2007/0003507 | A1 | 1/2007 | Mougin et al. | FR | 2 775 566 | 9/1999 |
| 2007/0166259 | A1 | 7/2007 | Vicic et al. | FR | 2 775 593 | 9/1999 |
| 2008/0014232 | A1 | 1/2008 | Arnaud et al. | FR | 2 791 042 | 9/2000 |
| 2008/0050329 | A1 | 2/2008 | De La Poterie | FR | 2 791 987 | 10/2000 |
| 2008/0069793 | A1 | 3/2008 | Loffler et al. | FR | 2 791 988 | 10/2000 |
| 2008/0107617 | A1 | 5/2008 | Loffler et al. | FR | 2 792 190 | 10/2000 |
| 2008/0159965 | A1 | 7/2008 | Mougin et al. | FR | 2 792 618 | 10/2000 |
| 2008/0207773 | A1 | 8/2008 | Loffler et al. | FR | 2 798 061 | 3/2001 |
| 2008/0219943 | A1 | 9/2008 | De La Poterie | FR | 2 803 743 | 7/2001 |
| | | | | FR | 2 806 273 | 9/2001 |
| | FOREIGN PATENT DOCUMENTS | | | FR | 2 296 402 | 11/2001 |
| | | | | FR | 2 809 306 | 11/2001 |
| DE | 100 22 247 | | 11/2001 | FR | 2 811 993 | 1/2002 |
| DE | 100 29 697 | | 12/2001 | FR | 2 814 365 | 3/2002 |
| EP | 1 279 398 | | 9/1971 | FR | 2 816 503 | 5/2002 |
| EP | 0 080 976 | | 6/1983 | FR | 2 823 101 | 10/2002 |
| EP | 0 295 886 | | 12/1988 | FR | 2 823 103 | 10/2002 |
| EP | 0 320 218 | | 6/1989 | FR | 2 827 514 | 1/2003 |
| EP | 0 173 109 | | 10/1989 | FR | 2 831 430 | 5/2003 |
| EP | 0 388 582 | | 9/1990 | FR | 2 832 719 | 5/2003 |
| EP | 0 412 704 | | 2/1991 | FR | 2 832 720 | 5/2003 |
| EP | 0 412 707 | | 2/1991 | FR | 2 834 458 | 7/2003 |
| EP | 0 549 494 | | 6/1993 | FR | 2 840 205 | 12/2003 |
| EP | 0 582 152 | | 2/1994 | FR | 2 840 209 | 12/2003 |
| EP | 0 216 479 | | 8/1994 | FR | 2 842 417 | 1/2004 |
| EP | 0 619 111 | | 10/1994 | FR | 2 844 709 | 3/2004 |
| EP | 0 637 600 | | 2/1995 | FR | 2 860 143 | 4/2005 |
| EP | 0 648 485 | | 4/1995 | FR | 2 860 156 | 4/2005 |
| EP | 0 656 021 | | 6/1995 | FR | 2 880 268 | 7/2006 |
| EP | 0 667 146 | | 8/1995 | GB | 0 839 805 | 6/1960 |
| EP | 0 550 745 | | 9/1995 | GB | 0 922 457 | 4/1963 |
| EP | 0 686 858 | | 12/1995 | GB | 1 021 400 | 3/1966 |
| EP | 0 750 031 | | 12/1996 | GB | 1 169 862 | 11/1969 |
| EP | 0 751 162 | | 1/1997 | GB | 1 324 745 | 7/1973 |
| EP | 0 751 170 | | 1/1997 | GB | 1 331 819 | 9/1973 |
| EP | 0 815 836 | | 1/1998 | GB | 1 407 659 | 9/1975 |
| EP | 0 847 752 | | 6/1998 | GB | 1 572 626 | 7/1980 |
| EP | 0 861 859 | | 9/1998 | JP | 5-221829 | 8/1993 |
| EP | 0 951 897 | | 10/1999 | JP | 06-279323 | 10/1994 |
| EP | 1 018 311 | | 7/2000 | JP | 07-196450 | 8/1995 |
| EP | 1 024 184 | | 8/2000 | JP | H07-309721 | 11/1995 |
| EP | 1 043 345 | | 10/2000 | JP | 07-324017 | 12/1995 |
| EP | 1 066 817 | | 1/2001 | JP | H08-119836 | 5/1996 |
| EP | 1 068 856 | | 1/2001 | JP | 09-263518 | 10/1997 |
| EP | 1 082 953 | | 3/2001 | JP | 10-506404 | 6/1998 |
| EP | 1 159 950 | | 12/2001 | JP | H11-100307 | 4/1999 |
| EP | 1 192 930 | | 4/2002 | JP | 11-124312 | 5/1999 |
| EP | 1 201 221 | | 5/2002 | JP | 2000-83728 | 3/2000 |
| EP | 1 356 799 | | 10/2003 | JP | 2000-319325 | 11/2000 |
| EP | 1 366 741 | | 12/2003 | JP | 2000-319326 | 11/2000 |
| EP | 1 366 744 | | 12/2003 | JP | 2001-348553 | 12/2001 |
| EP | 1 366 746 | | 12/2003 | JP | 2001-527559 | 12/2001 |
| EP | 1 411 069 | | 4/2004 | JP | 2002-201110 | 7/2002 |
| EP | 0 955 039 | | 5/2004 | JP | 2002-201244 | 7/2002 |
| EP | 1 421 928 | | 5/2004 | JP | 2003-40336 | 2/2003 |
| EP | 1 440 680 | | 7/2004 | JP | 2003-73222 | 3/2003 |
| EP | 1 518 534 | | 3/2005 | | | |

| | | |
|---|---|---|
| JP | 2003-081742 | 3/2003 |
| JP | 2003-286142 | 10/2003 |
| JP | 2004-002432 | 1/2004 |
| JP | 2004-002435 | 1/2004 |
| JP | 2004-149772 | 5/2004 |
| JP | 2004-269497 | 9/2004 |
| JP | 2005-104979 | 4/2005 |
| JP | 2006-503921 | 3/2006 |
| JP | 2006-507355 | 3/2006 |
| JP | 2006-507365 | 3/2006 |
| JP | 2006-507366 | 3/2006 |
| JP | 2006-507367 | 3/2006 |
| JP | 2006-151867 | 6/2006 |
| LU | 75370 | 7/1976 |
| LU | 75371 | 7/1976 |
| WO | WO 93/01797 | 2/1993 |
| WO | WO 93/23009 | 11/1993 |
| WO | WO 93/23446 | 11/1993 |
| WO | WO 94/03510 | 2/1994 |
| WO | WO 95/00578 | 1/1995 |
| WO | WO 95/03776 | 2/1995 |
| WO | WO 95/06078 | 3/1995 |
| WO | WO 96/10044 | 4/1996 |
| WO | WO 97/17057 | 5/1997 |
| WO | WO 98/31329 | 7/1998 |
| WO | WO 98/38981 | 9/1998 |
| WO | WO 98/42298 | 10/1998 |
| WO | WO 98/44012 | 10/1998 |
| WO | WO 98/51276 | 11/1998 |
| WO | WO 00/26285 | 5/2000 |
| WO | WO 00/28948 | 5/2000 |
| WO | WO 00/40216 | 7/2000 |
| WO | WO 00/49997 | 8/2000 |
| WO | WO 01/03538 | 1/2001 |
| WO | WO 01/13863 | 3/2001 |
| WO | WO 01/19333 | 3/2001 |
| WO | WO 01/30886 | 5/2001 |
| WO | WO 01/43703 | 6/2001 |
| WO | WO 01/51018 | 7/2001 |
| WO | WO 01/89470 | 11/2001 |
| WO | WO 01/95871 | 12/2001 |
| WO | WO 02/05762 | 1/2002 |
| WO | WO 02/05765 | 1/2002 |
| WO | WO 02/28358 | 4/2002 |
| WO | WO 02/34218 | 5/2002 |
| WO | WO 02/067877 | 9/2002 |
| WO | WO 02/080869 | 10/2002 |
| WO | WO 03/018423 | 3/2003 |
| WO | WO 03/046032 | 6/2003 |
| WO | WO 03/046033 | 6/2003 |
| WO | WO 2004/022009 | 3/2004 |
| WO | WO 2004/022010 | 3/2004 |
| WO | WO 2004/024700 | 3/2004 |
| WO | WO 2004/028485 | 4/2004 |
| WO | WO 2004/028487 | 4/2004 |
| WO | WO 2004/028489 | 4/2004 |
| WO | WO 2004/028491 | 4/2004 |
| WO | WO 2005/030158 | 4/2005 |

OTHER PUBLICATIONS

Hansen, C. M., "The Three Dimensional Solubility Parameter—Key to Paint Component Affinities: I. Solvents, Plasticizers, Polymers, and Resins", Journal of Paint Technology, vol. 39, No. 505 pp. 104-117, (1967).
Copending U.S. Appl. No. 10/670,388.
Office Action of U.S. Appl. No. 10/670,388 dated Jan. 7, 2008.
Search Report for EP 03 29 2383 dated May 17, 2004.
English language Derwent Abstract of DE 100 29 697, Dec. 20, 2001.
English language Derwent Abstract of FR 2 140 977.
French Search Report for FR 02 11949, Jul. 7, 2003, (see NPL dated Sep. 26, 2003, in prior U.S. Appl. No. 10/670,478).
Aldrich: Polymer Properties; 4th Ed. Catalog No. Z41, 247-3 (1999) published by John Wiley, New York.
Boutevin, B. et al., "Study of Morphological and Mechanical Properties of PP/PBT," Polymer Bulletin, 34, pp. 117-123, (1995).
Buzin, A. et al., "Calorimetric Study of Block-Copolymers of Poly(n-butyl Acrylate) and Gradient Poly(n-butyl acrylate-co-methyl methacrylate)" vol. 43, 2002, pp. 5563-5569.
Co-pending U.S. Appl. No. 10/528,698, filed Mar. 22, 2005; Inventors: Veronique Ferrari et al.
Co-pending U.S. Appl. No. 10/528,699, filed Mar. 22, 2005; Inventors: Philippe Ilekti et al.
Co-pending U.S. Appl. No. 10/528,835, filed Mar. 23, 2005; Inventors: Xavier Blin et al.
Co-pending U.S. Appl. No. 10/529,218, filed Mar. 25, 2005; Inventors: Xavier Blin et al.
Co-pending U.S. Appl. No. 10/529,264, filed Mar. 25, 2005; Inventors: Veronique Ferrari et al.
Co-pending U.S. Appl. No. 10/529,265, filed Sep. 28, 2005; Inventors: Xavier Blin et al.
Co-pending U.S. Appl. No. 10/529,266, filed Mar. 25, 2005; Inventors: Xavier Blin et al.
Co-pending U.S. Appl. No. 10/529,267, filed Sep. 29, 2005; Inventors: Valerie De La Poterie et al.
Co-pending U.S. Appl. No. 10/529,318, filed Mar. 25, 2005; Inventors: Xavier Blin et al.
Co-pending U.S. Appl. No. 10/573,579, filed Dec. 26, 2006; Inventor: Marco Vicic et al.
Co-pending U.S. Appl. No. 10/585,817, filed Jan. 10, 2007; Inventor: Valerie De La Poterie.
Co-pending U.S. Appl. No. 10/585,818, filed Jul. 12, 2006; Inventors: Valerie De La Poterie.
Co-pending U.S. Appl. No. 10/670,478, filed Sep. 26, 2003; Inventors: Bertrand Lion et al.
Co-pending U.S. Appl. No. 10/949,435, filed Sep. 27, 2004; Inventors: Xavier Blin et al.
Co-pending U.S. Appl. No. 10/949,448, filed Sep. 27, 2004; Inventors: Xavier Blin et al.
Co-pending U.S. Appl. No. 11/086,906, filed Mar. 23, 2005; Inventors: Philippe Ilekti et al.
Co-pending U.S. Appl. No. 11/089,210, filed Mar. 25, 2005.
Co-pending U.S. Appl. No. 11/858,994, filed Sep. 21, 2007; Inventors: Bertrand Lion et al.
Co-pending U.S. Appl. No. 11/859,004, filed Sep. 21, 2007; Inventors: Bertrand Lion et al.
Co-pending U.S. Appl. No. 11/878,067, filed Jul. 20, 2007; Inventors: Caroline Lebre et al.
Co-pending U.S. Appl. No. 11/878,849, filed Jul. 27, 2007; Inventors: Celine Farcet et al.
Cortazar, M. et al., "Glass Transition Temperatures of Plasticized Polyarylate,", Polymer Bulletin 18, 149-154 (1987).
English Derwent Abstract for EP 1 082 953, dated Mar. 14, 2001.
English Derwent Abstract for EP 1 159 950, dated Dec. 5, 2001.
English Derwent Abstract for FR 2 798 061, dated Mar. 9, 2001.
English Derwent Abstract for FR 2 803 743, dated Jul. 20, 2001.
English Derwent Abstract for WO 01/03538, dated Jan. 18, 2001.
English Derwent Abstract for WO 04/028489, dated Apr. 8, 2004.
English language Abstract of EP 1 604 634, dated Dec. 14, 2005.
English language Abstract of FR 1 222 944, dated Jun. 14, 1960.
English language Abstract of FR 1 564 110, dated 1968.
English language Abstract of FR 2 357 241, dated Feb. 3, 1978.
English language Abstract of FR 2 834 458, dated Jul. 11, 2003.
English language Abstract of FR 2 880 268, dated Jul. 7, 2006.
English language Abstract of JP 2003-40336, Feb. 13, 2003.
English language Abstract of JP 2006-151867, dated Jun. 15, 2006.
English language Derwent Abstract for EP 0 080 976, dated Jun. 8, 1983.
English language Derwent Abstract for FR 2 775 566, dated Sep. 10, 1999.
English language Derwent Abstract for FR 2 792 190, dated Oct. 20, 2000.
English language Derwent Abstract for FR 2 831 430, dated May 2, 2003.
English language Derwent Abstract for JP 06-279323, dated Oct. 4, 1994.
English language Derwent Abstract for JP 07-196450, dated Aug. 1, 1995.
English language Derwent Abstract for JP 09-263518, dated Oct. 7, 1997.
English language Derwent Abstract for JP 11-124312, dated May 11, 1999.

English language Derwent Abstract of EP 0 648 485, dated Apr. 19, 1995.
English language Derwent Abstract of FR 2 860 156, Apr. 1, 2005.
English language Derwent Abstract of JP 2001-348553, Dec. 18, 2001.
English language Derwent Abstract of JP 2002-201244, dated Jul. 19, 2002.
English language Derwent Abstract of JP 2004-002432, Jan. 8, 2004.
English language Derwent Abstract of JP 2004-002435, Jan. 8, 2004.
English language Derwent Abstract of JP 5-221829, dated Aug. 31, 1993.
Erichsen, J. et al., "Molecular Weight Dependence of the Surface Glass Transition of Polystyrene Films Investigated by the Embedding of Gold Nanoclusters," MRS Publication, 2001.
Flick, "Cosmetic Additives: An Industrial Guide", Noyes Publications, Park Ridge, NJ, p. 266 (1991).
Fonnum, et al., "Associative Thickeners. Part I: Synthesis, Rheology and Aggregation Behavior," Colloid & Polym. Sci., 1993, 271: 380-389.
French Search Report for FR 03/11340 for Copending U.S. Appl. No. 10/949,448, dated May 9, 2005.
French Search Report for FR 04/03088, for co-pending U.S. Appl. No. 11/089,172 dated Nov. 2, 2004.
French Search Report for FR 04/03090, for co-pending U.S. Appl. No. 11/089,210, dated Sep. 30, 2004.
French Search Report for FR 04/50572, for Copending U.S. Appl. No. 11/086,906, dated Nov. 9, 2004.
French Search Report for Fr 06/53144, for co-pending U.S. Application No. 11/878,849, dated Feb. 13, 2007.
French Search Report for FR 06/53154, for co-pending U.S. Appl. No. 11/878,067, dated Apr. 2, 2007.
Hamley, I.W., "Crystallization in Block Copolymers," Advances in Polymer Science, vol. 148, pp. 113-137 (1999).
HCAPLUS abstract 1964: 70247, abstracting: Develop. Ind. Microbiol., vol. 2, pp. 47-53 (1961).
International Search Report for PCT Application No. PCT/FR03/02849 (Priority Application for U.S. Appl. No. 10/529,265), dated Jun. 24, 2004.
International Search Report for PCT/FR03/002844 (Priority Application for U.S. Appl. No. 10/529,318), dated May 14, 2005.
International Search Report for PCT/FR03/002847 (Priority Application for U.S. Appl. No. 10/529,266), dated May 17, 2004.
International Search Report for PCT/FR03/02841 (Priority Application for U.S. Appl. No. 10/529,267), dated Jun. 1, 2004.
International Search Report for PCT/FR03/02842 (Priority Application for U.S. Appl. No. 10/529,218), dated May 17, 2004.
International Search Report for PCT/FR03/02843 (Priority Application for U.S. Appl. No. 10/528,698), dated May 17, 2004.
International Search Report for PCT/FR03/02845 (Priority Application for U.S. Appl. No. 10/529,264), dated May 17, 2004.
International Search Report for PCT/FR03/02846 (Priority Application for U.S. Appl. No. 10/528,699), dated May 17, 2004.
International Search Report for PCT/FR03/02848 (Priority Application for U.S. Appl. No. 10/528,835), dated May 17, 2004.
International Search Report for PCT/IB2005/000230 (Priority Application for U.S. Appl. No. 10/585,817), dated May 27, 2005.
International Search Report for PCT/IB2005/000236 (Priority Application for U.S. Appl. No. 10/585,818), dated Aug. 3, 2005.
Kirk-Othmer, "Encyclopedia of Chemical Technology", vol. 22, 3rd Edition, Wiley, 1979, pp. 333-432.
Nojima, S., "Melting Behavior of Poly (E-caprolactone)-block-polybutadiene Copolymers", Macromolecules, 32, 3727-3734 (1999).
Nojiri, A. et al., "Molecular Weight Dependence of the Glass Transition Temperature in Poly(vinyl acetate)," Japan J. Appl. Phys. 10 (1971), p. 803.
Office Action mailed Apr. 28, 2010, in co-pending U.S. Appl. No. 10/528,835.
Office Action mailed Aug. 12, 2005, in co-pending U.S. Appl. No. 10/670,478.
Office Action mailed Aug. 12, 2009 in co-pending U.S. Appl. No. 10/949,448.
Office Action mailed Aug. 18, 2009 in co-pending U.S. Appl. No. 10/529,264.
Office Action mailed Dec. 10, 2008, in co-pending U.S. Appl. No. 10/528,698.
Office Action mailed Dec. 23, 2008, in co-pending U.S. Appl. No. 10/529,266.
Office Action mailed Dec. 29, 2009 in co-pending U.S. Appl. No. 10/529,265.
Office Action mailed Dec. 3, 2009 in co-pending U.S. Appl. No. 10/528,698.
Office Action mailed Feb. 2, 2010, in co-pending U.S. Appl. No. 10/949,448.
Office Action mailed Feb. 27, 2009, in co-pending U.S. Appl. No. 11/878,849.
Office Action mailed Jan. 28, 2010, in co-pending U.S. Appl. No. 10/529,264.
Office Action mailed Jul. 21, 2009, in co-pending U.S. Appl. No. 11/878,067.
Office Action mailed Jun. 12, 2009 in co-pending U.S. Appl. No. 11/086,906.
Office Action mailed Jun. 24, 2009 in co-pending U.S. Appl. No. 10/528,698.
Office Action mailed Jun. 24, 2009 in co-pending U.S. Appl. No. 10/529,267.
Office Action mailed Jun. 29, 2009 in co-pending U.S. Appl. No. 10/529,266.
Office Action mailed Jun. 4, 2009 in co-pending U.S. Appl. No. 10/670,478.
Office Action mailed Jun. 8, 2009 in co-pending U.S. Appl. No. 11/089,210.
Office Action mailed Mar. 12, 2009, in co-pending U.S. Appl. No. 10/529,218.
Office Action mailed Mar. 17, 2010, in co-pending U.S. Appl. No. 10/529,318.
Office Action mailed Mar. 18, 2009, in co-pending U.S. Appl. No. 10/528,699.
Office Action mailed Mar. 18, 2009, in co-pending U.S. Appl. No. 10/573,579.
Office Action mailed Mar. 18, 2009, in related U.S. Appl. No. 11/089,172.
Office Action mailed Mar. 26, 2008, in co-pending U.S. Appl. No. 10/670,478.
Office Action mailed Mar. 30, 2010, in co-pending U.S. Appl. No. 11/089,210.
Office Action mailed Mar. 30, 2010, in co-pending U.S. Appl. No. 11/878,067.
Office Action mailed Mar. 7, 2006, in co-pending U.S. Appl. No. 10/670,478.
Office Action mailed May 3, 2007, in co-pending U.S. Appl. No. 10/670,478.
Office Action mailed Nov. 15, 2006, in co-pending U.S. Appl. No. 10/670,478.
Office Action mailed Nov. 17, 2009 in co-pending U.S. Appl. No. 10/528,835.
Office Action mailed Nov. 25, 2008, in co-pending U.S. Appl. No. 10/949,448.
Office Action mailed Nov. 25, 2008, in co-pending U.S. Appl. No. 10/670,388.
Office Action mailed Nov. 6, 2009 in co-pending U.S. Appl. No. 10/949,435.
Office Action mailed Oct. 1, 2008, in co-pending U.S. Appl. No. 10/529,318.
Office Action mailed Oct. 21, 2008, in co-pending U.S. Appl. No. 10/670,478.
Office Action mailed Oct. 27, 2009 in co-pending U.S. Appl. No. 10/529,218.
Office Action mailed Sep. 2, 2009 in co-pending U.S. Appl. No. 10/529,318.
Office Action mailed Sep. 28, 2009 in co-pending U.S. Appl. No. 10/670,478.
Office Action mailed Sep. 7, 2007, in co-pending U.S. Appl. No. 10/670,478.

Office Action mailed Sep. 9, 2009, in co-pending U.S. Appl. No. 11/878,849.

Pigeon, R. et al., Chimie Macromoleculaire Appliquee, No. 600, 40/41 (1974), pp. 139-158, Abstract.

Porter, "Chapter 7: Non Ionics," Handbook of Surfactants, 1991, pp. 116-178, Chapman and Hall, New York.

Prince, L.M. ed., Macroemulsions Theory and Practice, Academic Press (1977), pp. 21-32.

Rangarajan P., et al., "Morphology of Semi-Crystalline Block Copolymers of Ethylene-(ethylene-alt-propylene)," Macromolecules, 26, 4640-4645 (1993).

Related U.S. Appl. No. 11/089,172, filed Mar. 25, 2005, Inventors: Katarina Benabdillah et al.

Richter, P. et al., "Polymer Aggregates with Crystalline Cores: The System Poly(ethylene)-poly(ethylene-propylene)," Macromolecules, 30, 1053-1068 (1997).

Specific Gravity and Viscosity of Liquid Table; available at http://www.csgnetwork.com/sgvisc.html. Sesame seed oil information originally published Mar. 28, 2002.

Thermal_Transisitons_of_Homopolymers.pdf. Thermal Transistions of Homopolymers: Glass Transistion & Melting Point Data. Accessed online Dec. 19, 2008 at: http://www.sigmaaldrich.com/etc/medialib/docs/Aldrich/General_Information/thermal_transitions_of_homopolymers.Par.0001.File.tmp/thermal_transitions_of_homopolymers.pdf.

Toniu, P. et al., "Process for Preparation of Block Polymers, Products Obtained by Means of the Process and Cosmetic Compositions Containing Them", 1973, French Patent Office, pp. 1-26 (English translation of French Patent No. FR2140977).

Notice of Allowance in U.S. Appl. No. 10/670,478 dated Jul. 6, 2010.

Office Action mailed Aug. 2, 2010, in co-pending U.S. Appl. No. 10/949,435.

Office Action mailed Aug. 31, 2010, in co-pending U.S. Appl. No. 10/529,265.

Office Action mailed Jul. 12, 2010, in co-pending U.S. Appl. No. 11/858,994.

Office Action mailed Jul. 28, 2010, in co-pending U.S. Appl. No. 10/529,264.

Office Action mailed Jul. 9, 2010, in co-pending U.S. Appl. No. 11/859,004.

Office Action mailed May 12, 2010, in co-pending U.S. Appl. No. 11/086,906.

Office Action mailed May 28, 2010, in co-pending U.S. Appl. No. 10/573,579.

BLOCK POLYMERS AND COSMETIC COMPOSITIONS AND PROCESSES COMPRISING THEM

This is a divisional application of application Ser. No. 10/670,478, filed Sep. 26, 2003, which claims the benefit of French Patent Application No. 02 11949, filed Sep. 26, 2002, now U.S. Pat. No. 7,803,877 and French Patent Application No. 03 06121, filed May 21, 2003, all of which are incorporated herein by reference.

This application claims priority under 35 U.S.C. §119 to French Patent Application Nos. 0211949, filed Sep. 9, 2002, and 02306121, filed May 21, 2003, both of which are hereby incorporated by reference.

The present invention relates to novel polymers of specific structure.

The present invention also relates to cosmetic compositions comprising such polymers.

Various types of polymers are conventionally used in cosmetic compositions because of the various properties that they can give to these compositions.

Polymers are used, for example, in makeup or care compositions for the skin, the lips, or the integuments, such as nail varnishes or haircare compositions.

However, when a formulator is using two polymers that are incompatible, i.e., immiscible in the same solvent, within the same composition, the formulator is confronted with problems of phase separation or decantation, and in general with the production of a non-uniform composition. These problems could only be solved hitherto by the presence in the composition of a compound for rendering the polymers mutually compatible.

The present inventors thus proposes a polymer which, when included in a composition, for example a cosmetic composition, enables the composition to avoid the drawbacks, limitations, defects and disadvantages of the compositions of the prior art.

The inventors have found that these drawbacks, limitations, defects, or disadvantages may be avoided by means of a polymer, referred to as a block polymer, comprising at least one first block and at least one second block that are incompatible with each other and that have different glass transition temperatures (Tg), the at least one first and at least one second blocks being linked together via at least one intermediate segment comprising at least one constituent monomer of the at least one first block and at least one constituent monomer of the at least one second block, and where the polymer has a polydispersity index I of greater than 2.

The expression "at least one block" means one or more blocks.

The expression blocks "that are incompatible with each other" means that the mixture of the polymer formed by the at least one first block and the polymer formed by the at least one second block (hereinafter referred to as "the polymer mixture") is immiscible in the main polymerization organic solvent of the block copolymer at room temperature (25° C.) and atmospheric pressure ($10^5$ Pa), at a content of the polymer mixture greater or equal to 5% by weight of the total weight of polymers and solvent, and wherein
(i) the polymer formed by the at least one first block and the polymer formed by the at least one second block are present in the polymer mixture in a ratio ranging from 10/90 to 90/10 by weight, and
(ii) each of the polymer formed by the at least one first block and the polymer formed by the at least one second block has an average molar mass (weight-average or number-average molar mass) equal to the average mass of the block polymer+/−15%.

The expression "main polymerization organic solvent" means, in the case where there is a mixture of polymerization solvents, the polymerization solvent which has the highest content by weight relative to the total weight of the organic polymerization solvents. In the case where there is a mixture of polymerization solvents and two or more of the solvents are present in identical weight ratios, the polymer mixture is immiscible in at least one of the solvents. In the case where the polymerization is made in a single solvent, the single solvent is the main solvent.

The at least one intermediate segment is a block comprising at least one constituent monomer of the at least one first block and at least one constituent monomer of the at least one second block of the polymer and allows these blocks to be "compatibilized."

By incorporating these novel polymers into cosmetic compositions, the present inventors have discovered that some of these polymers, described in greater detail below, may have advantageous cosmetic properties. In general, these polymers may be incorporated into compositions to a high solids content, for example greater than 10% by weight relative to the total weight of the composition, and are easy to formulate. When used in haircare products, they may improve at least one of styling power and suppleness. They may increase the impact strength of nail varnishes and may improve the staying power of a wide variety of makeup compositions without causing the user any discomfort.

Disclosed herein is also a cosmetic composition comprising such a polymer.

Further disclosed herein is a cosmetic makeup or care process for keratin materials, comprising applying to the keratin materials a cosmetic composition as disclosed herein.

Also disclosed is a method for improving the staying power of a composition comprising providing a polymer as disclosed herein in a cosmetic composition, as an agent for improving the staying power of the composition.

Finally, disclosed herein is the use of the polymer as disclosed in a composition with improved staying power properties.

In one embodiment, the block polymer of the composition disclosed herein may be a film-forming linear block ethylene polymer.

The term "ethylene polymer" as defined herein is understood to mean a polymer obtained by the polymerization of monomers containing an ethylenically unsaturated group.

The term "block polymer" is understood to mean a polymer comprising at least two separate blocks, for example, at least three separate blocks.

The polymer may be a polymer with a linear structure. In contrast, a polymer having a non-linear structure may be, for example, a polymer with a branched, star, grafted, or other structure.

The term "film-forming polymer" is understood to mean a polymer capable of forming, by itself or in the presence of at least one auxiliary film-forming agent, a continuous film that adheres to a support, for example, to keratinous materials.

In one embodiment, the polymer disclosed herein does not comprise any silicon atoms in its skeleton. The term "skeleton" means the main chain of the polymer, as opposed to the pendent side chains.

In one embodiment, the polymer disclosed herein may not be water-soluble, that is to say the polymer may not be soluble in water or in a mixture of water and linear or branched lower monoalcohols having from 2 to 5 carbon atoms, chosen from ethanol, isopropanol, and n-propanol, without pH modification, with an active material content of less than 1% by weight, at room temperature (25° C.).

In one embodiment, the polymer disclosed herein may not be water-soluble, i.e., the polymer may not be soluble in water or in a mixture of water and hydrophilic organic solvent(s) without pH modification, with an active material content of at least 1% by weight, at room temperature (25° C.).

The expression "hydrophilic organic solvent" means alcohols and for example linear and branched lower monoalcohols containing from 2 to 5 carbon atoms, for example ethanol, isopropanol, and n-propanol, and polyols, for example glycerol, diglycerol, propylene glycol, sorbitol, and pentylene glycol, and polyethylene glycols, hydrophilic $C_2$ ethers, and $C_2$-$C_4$ aldehydes.

In one embodiment, the polymer disclosed herein is not an elastomer.

The expression "non-elastomeric polymer" means a polymer which, when submitted to a stretching stress (for example when stretched by 30% of the original length) does not return to approximately its original length when released. Specifically, "non-elastomeric polymer" means a polymer with an instantaneous recovery $R_i$<50% and a delayed recovery $R_{2h}$<70% after having undergone a 30% elongation. In one embodiment, $R_i$ is <30% and $R_{2h}$ is <50%.

The elastomeric nature of the polymer may be determined according to the following protocol:

A polymer film is prepared by pouring a solution of the polymer into a Teflon-coated mold followed by drying for 7 days under ambient conditions regulated to 23±5° C. and 50±10% relative humidity.

A film about 100 µm thick is thus obtained, from which are cut for example, rectangular specimens (for example using a punch) 15 mm wide and 80 mm long.

This sample is subjected to a tensile stress using a machine sold under the reference Zwick, under the same temperature and humidity conditions as for the drying operation.

The specimens are drawn at a speed of 50 mm/minute and the distance between the jaws is 50 mm, which corresponds to the initial length (Lo) of the specimen.

The instantaneous recovery $R_i$ is determined in the following manner:
- the specimen is stretched by 30% ($\epsilon_{max}$), i.e. about 0.3 times its initial length (Lo)
- the stress is released by applying a return speed equal to the tensile speed, i.e., 50 mm/minute, and the residual elongation percentage of the specimen, after returning to zero stress ($\epsilon_i$), is measured.

The percentage instantaneous recovery ($R_i$) is given by the formula below:

$$R_i = ((\epsilon_{max} - \epsilon_i)/\epsilon_{max}) \times 100$$

To determine the delayed recovery, the residual percentage degree of elongation of the specimen ($\epsilon_{2h}$) is measured 2 hours after returning to zero stress.

The delayed recovery in % ($R_{2h}$) is given by the formula below:

$$R_{2h} = ((\epsilon_{max} - \epsilon_{2h})/\epsilon_{max}) \times 100$$

For example, in one embodiment, the polymer has an instantaneous recovery $R_i$ of 10% and a delayed recovery $R_{2h}$ of 30%

The polymer disclosed herein comprises at least one first block and at least one second block that are incompatible with each other and that have different glass transition temperatures (Tg), the at least one first and second blocks are linked together via at least one intermediate segment comprising at least one constituent monomer of the at least one first block and at least one constituent monomer of the at least one second block, the polymer having a polydispersity index I of greater than 2.

It is pointed out that, in the text hereinabove and hereinbelow, the terms "first" and "second" blocks do not in any way condition the order of the blocks in the structure of the polymer.

The polydispersity index I of the polymer may be equal to the ratio of the weight-average mass Mw to the number-average mass Mn.

The weight-average (Mw) and number-average (Mn) molar masses are determined by gel permeation liquid chromatography (THF solvent, calibration curve established with linear polystyrene standards, refractometric detector).

The weight-average mass (Mw) of the polymer disclosed herein may be, for example, less than or equal to 300 000, for example ranging from 35 000 to 200 000, and as a further example, from 45 000 to 150 000.

The number-average mass (Mn) of the polymer disclosed herein may be, for example, less than or equal to 70 000, for example ranging from 10 000 to 60 000, and as a further example, ranging from 12 000 to 50 000.

The polydispersity index of the polymer disclosed herein may be greater than 2, for example ranging from 2 to 9, in one embodiment greater than or equal to 2.5, for example ranging from 2.5 to 8, and in another embodiment greater than or equal to 2.8, and for example ranging from 2.8 to 6.

Each block of the polymer disclosed herein may be derived from one type of monomer or from several different types of monomers. This means that each block may comprise a homopolymer or a copolymer. The copolymer constituting the block may in turn be random or alternating.

In one embodiment, the at least one intermediate segment comprising at least one constituent monomer of the at least one first block and at least one constituent monomer of the at least one second block of the polymer is a random polymer.

For example, the at least one intermediate segment may be at least 85% derived from constituent monomers of the at least one first block and of the at least one second block, as a further example at least 90%, in another example 95%, and as another example 100%.

In one embodiment, the at least one intermediate segment has a glass transition temperature Tg that is between the glass transition temperatures of the at least one first and at least one second blocks.

As disclosed herein, the at least one first and second blocks may have different glass transition temperatures.

The glass transition temperatures indicated for the at least one first and second blocks may be theoretical Tg values determined from the theoretical Tg values of the constituent monomers of each of the blocks, which may be found in a reference manual for example, the Polymer Handbook, 3rd Edition, 1989, John Wiley, which is hereby incorporated by reference, according to the following relationship, known as Fox's law:

$$1/Tg = \sum_i (\overline{\omega}_i / Tg_i),$$

$\overline{\omega}_i$ being the mass fraction of the monomer i in the block under consideration and $Tg_i$ being the glass transition temperature of the homopolymer of the monomer i.

Unless otherwise indicated, the Tg values indicated for the at least one first and second blocks are theoretical Tg values.

The difference between the glass transition temperatures of the at least one first and second blocks may be generally greater than 10° C., for example greater than 20° C., and as a further example greater than 30° C.

In one embodiment, the at least one first block may be chosen from:
a) a block with a Tg of greater than or equal to 40° C.
b) a block with a Tg of less than or equal to 20° C.,
c) a block with a Tg of between 20 and 40° C.
and the at least one second block is chosen from a block of category a), b) or c) that may be different from the first block.

As used herein, the expression "between . . . and . . . " is intended to denote a range of values for which the limits mentioned are excluded, and "from . . . to . . . " and "ranging from . . . to . . . " are intended to denote a range of values for which the limits are included.

a) Block with a Tg of Greater than or Equal to 40° C.

The block with a Tg of greater than or equal to 40° C. has, for example, a Tg ranging from 40 to 150° C., in another embodiment greater than or equal to 50° C., for example ranging from 50° C. to 120° C., as a further example, ranging from 50° C. to 100° C., and in a further embodiment greater than or equal to 60° C., for example ranging from 60° C. to 120° C.

The block with a Tg of greater than or equal to 40° C. may be a homopolymer or a copolymer.

In the case where this block is a homopolymer, it may be derived from at least one monomer wherein a homopolymer prepared from the at least one monomer has a glass transition temperature of greater than or equal to 40° C. This first block may be a homopolymer comprising one type of monomer (for which the Tg of the corresponding homopolymer is greater than or equal to 40° C.).

In the case where the at least one first block is a copolymer, it may be totally or partially derived from at least one monomer, the nature and concentration of which are chosen so that the Tg of the resulting copolymer is greater than or equal to 40° C. The copolymer may comprise, for example:
monomers wherein the homopolymers prepared from these monomers have Tg values of greater than or equal to 40° C., for example a Tg ranging from 40 to 150° C., in one embodiment greater than or equal to 50° C., for example ranging from 50° C. to 120° C., as a further example ranging from 50° C. to 100° C. and in another embodiment greater than or equal to 60° C., for example ranging from 60° C. to 120° C., and
monomers wherein the homopolymers prepared from these monomers have Tg values of less than 40° C., chosen from monomers with a Tg of between 20 and 40° C. and/or monomers with a Tg of less than or equal to 20° C., for example a Tg ranging from −100 to 20° C., in another embodiment less than or equal to 15° C., for example ranging from −80° C. to 15° C., and in another embodiment less than or equal to 10° C., for example ranging from −100° C. to 0° C., and as a further example ranging from −50° C. to 0° C., as described below.

The monomers whose homopolymers have a glass transition temperature of greater than or equal to 40° C. are chosen, for example, from the following monomers, also known as the main monomers:
methacrylates of formula $CH_2=C(CH_3)-COOR_1$
wherein $R_1$ is chosen from linear and branched unsubstituted alkyl groups comprising from 1 to 4 carbon atoms, from methyl, ethyl, propyl, and isobutyl groups and from $C_4$ to $C_{12}$ cycloalkyl groups,
acrylates of formula $CH_2=CH-COOR_2$
wherein $R_2$ is chosen from $C_4$ to $C_{12}$ cycloalkyl groups chosen from an isobornyl group and a tert-butyl group, (meth)acrylamides of formula:

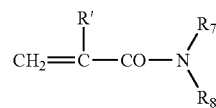

wherein $R_7$ and $R_8$, which may be identical or different, each are chosen from a hydrogen atom, linear and branched $C_1$ to $C_{12}$ alkyl groups such as n-butyl, t-butyl, isopropyl, isohexyl, isooctyl, and isononyl groups; or $R_7$ is H and $R_8$ is a 1,1-dimethyl-3-oxobutyl group,
and R' is chosen from H and methyl. Examples of monomers that may be mentioned include N-butylacrylamide, N-t-butylacrylamide, N-isopropylacrylamide, N,N-dimethylacrylamide and N,N-dibutylacrylamide,
and mixtures thereof.

Examples of useful main monomers include methyl methacrylate, isobutyl(meth)acrylate, isobornyl(meth)acrylate, and mixtures thereof.

b) Block with a Tg of Less than or Equal to 20° C.

The block with a Tg of less than or equal to 20° C. has, for example, a Tg ranging from −100 to 20° C., in another embodiment less than or equal to 15° C., for example ranging from −80° C. to 15° C., and in another embodiment less than or equal to 10° C., for example ranging from −100° C. to 0° C., and as a further example ranging from −50° C. to 0° C.

The block with a Tg of less than or equal to 20° C. may be a homopolymer or a copolymer.

In the case where this block is a homopolymer, it may be derived from at least one monomer wherein the homopolymers prepared from the at least one monomer has a glass transition temperature of less than or equal to 20° C. This second block may be a homopolymer comprising one type of monomer (for which the Tg of the corresponding homopolymer is less than or equal to 20° C.).

In the case where the block with a Tg of less than or equal to 20° C. is a copolymer, it may be totally or partially derived from at least one monomer, the nature and concentration of which are chosen so that the Tg of the resulting copolymer is less than or equal to 20° C.

It may comprise, for example
at least one monomer whose corresponding homopolymer has a Tg of less than or equal to 20° C., for example a Tg ranging from −100° C. to 20° C., in another embodiment less than or equal to 15° C., for example ranging from −80° C. to 15° C., and in another embodiment less than or equal to 10° C., for example ranging from −100° C. to 0° C. and as a further example ranging from −50° C. to 0° C., and
at least one monomer whose corresponding homopolymer has a Tg of greater than 20° C., for example monomers with a Tg of greater than or equal to 40° C., for example a Tg ranging from 40 to 150° C., in another embodiment greater than or equal to 50° C., for example ranging from 50° C. to 120° C., as a further example ranging from 50° C. to 100° C., and in another embodiment greater than or equal to 60° C., for example ranging from 60° C. to 120° C. and/or monomers with a Tg of between 20 and 40° C., as described above.

In one embodiment, the block with a Tg of less than or equal to 20° C. is a homopolymer.

The monomers whose homopolymer has a Tg of less than or equal to 20° C. may be, for example, chosen from the following monomers, or main monomer:

acrylates of formula $CH_2$=$CHCOOR_3$,
  wherein $R_3$ is chosen from linear and branched $C_1$ to $C_{12}$ unsubstituted alkyl groups, with the exception of the tert-butyl group, wherein at least one heteroatom chosen from O, N and S is (are) optionally intercalated, methacrylates of formula $CH_2$=$C(CH_3)$—$COOR_4$,
  wherein $R_4$ is chosen from linear and branched $C_6$ to $C_{12}$ unsubstituted alkyl groups, wherein at least one heteroatom chosen from O, N and S is (are) optionally intercalated, vinyl esters of formula $R_5$—CO—O—CH=$CH_2$
  wherein $R_5$ is chosen from linear and branched $C_4$ to $C_{12}$ alkyl groups, $C_4$ to $C_{12}$ alcohol and vinyl alcohols, N—($C_4$ to $C_{12}$)alkyl acrylamides, for example N-octylacrylamide, and mixtures thereof.

The main monomers for the block with a Tg of less than or equal to 20° C. may be, for example, alkyl acrylates whose alkyl chain contains from 1 to 10 carbon atoms, with the exception of the tert-butyl group, chosen from methyl acrylate, isobutyl acrylate, 2-ethylhexyl acrylate, and mixtures thereof.

c) Block with a Tg of Between 20 and 40° C.

The block with a Tg of between 20 and 40° C. may be a homopolymer or a copolymer.

In the case where this block is a homopolymer, it may be derived from at least one monomer (or main monomer) wherein the homopolymers prepared from the at least one monomer has a glass transition temperature of between 20 and 40° C. This first block may be a homopolymer comprising one type of monomer (for which the Tg of the corresponding homopolymer ranges from 20° C. to 40° C.).

The at least one monomer whose homopolymer has a glass transition temperature of between 20 and 40° C. may be, for example, chosen from n-butyl methacrylate, cyclodecyl acrylate, neopentyl acrylate, and isodecylacrylamide.

In the case where the block with a Tg of between 20 and 40° C. is a copolymer, it may be totally or partially derived from at least one monomer (or main monomer) whose nature and concentration are chosen so that the Tg of the resulting copolymer is between 20 and 40° C.

The block with a Tg of between 20 and 40° C. may be a copolymer totally or partially derived from:

main monomers whose corresponding homopolymer has a Tg of greater than or equal to 40° C., for example a Tg ranging from 40° C. to 150° C., in another embodiment greater than or equal to 50° C., for example ranging from 50 to 120° C., as a further example ranging from 50° C. to 100° C., and in another embodiment greater than or equal to 60° C., for example ranging from 60° C. to 120° C., as described above, and/or main monomers whose corresponding homopolymer has a Tg of less than or equal to 20° C., for example a Tg ranging from −100 to 20° C., in another embodiment less than or equal to 15° C., for example ranging from −80° C. to 15° C., and in another embodiment less than or equal to 10° C., for example ranging from −100° C. to 0° C., and as a further example ranging from −50° C. to 0° C., as described above, the at least one monomer may be chosen so that the Tg of the copolymer forming the at least one first block is between 20 and 40° C.

The main monomers may be chosen, for example, from methyl methacrylate, isobornyl acrylate, methacrylate, butyl acrylate, 2-ethylhexyl acrylate, and mixtures thereof.

In one embodiment, the at least one second block with a Tg of less than or equal to 20° C. is present in an amount ranging from 10% to 85% by weight, in another embodiment from 20% to 70%, and in another embodiment from 20% to 50% by weight of the block polymer.

However, each of the at least one first and second blocks may contain in small proportion at least one constituent monomer of the other at least one first and second block. Thus, the at least one first block may contain at least one constituent monomer of the at least one second block, and vice versa.

Each of the at least one first and/or second blocks may comprise, in addition to the at least one monomer indicated above, at least one other monomer known as an at least one additional monomer, which may be different from the main monomers mentioned above.

The nature and amount of this at least one additional monomer may be chosen so that the at least one first and second block in which they may be present has the desired glass transition temperature.

This at least one additional monomer may be chosen, for example, from:

a) hydrophilic monomers chosen from:

ethylenically unsaturated monomers comprising at least one carboxylic or sulphonic acid function, for example:

acrylic acid, methacrylic acid, crotonic acid, maleic anhydride, itaconic acid, fumaric acid, maleic acid, acrylamidopropanesulphonic acid, vinylbenzoic acid, vinylphosphoric acid, and salts thereof, ethylenically unsaturated monomers comprising at least one tertiary amine function, for example 2-vinylpyridine, 4-vinylpyridine, dimethylaminoethyl methacrylate, diethylaminoethyl methacrylate, dimethylaminopropylmethacrylamide, and salts thereof, methacrylates of formula $CH_2$=$C(CH_3)$—$COOR_6$
wherein $R_6$ may be chosen from linear and branched alkyl groups comprising from 1 to 4 carbon atoms, chosen from methyl, ethyl, propyl and isobutyl groups, the alkyl group being substituted with at least one substituent chosen from hydroxyl groups (for instance 2-hydroxypropyl methacrylate and 2-hydroxyethyl methacrylate) and halogen atoms (Cl, Br, I or F), for example trifluoroethyl methacrylate, methacrylates of formula $CH_2$=$C(CH_3)$—$COOR_9$,
wherein $R_9$ may be chosen from linear and branched $C_6$ to $C_{12}$ alkyl groups wherein at least one heteroatom chosen from O, N and S is optionally intercalated, the alkyl group being substituted with at least one substituent chosen from hydroxyl groups and halogen atoms (Cl, Br, I or F);

acrylates of formula $CH_2$=$CHCOOR_{10}$,
wherein $R_{10}$ may be chosen from linear and branched $C_1$ to $C_{12}$ alkyl groups substituted with at least one substituent chosen from hydroxyl and halogen atoms (Cl, Br, I or F), such as 2-hydroxypropyl acrylate and 2-hydroxyethyl acrylate, or $R_{10}$ is chosen from ($C_1$-$C_{12}$)alkyl-O-POE (polyoxyethylene) with repetition of the oxyethylene unit 5 to 30 times, for example methoxy-POE, or $R_{10}$ is chosen from a polyoxyethylenated group comprising from 5 to 30 ethylene oxide units, b) ethylenically unsaturated monomers comprising at least one silicon atom, chosen from methacryloxypropyltrimethoxysilane and methacryloxypropyl-tris(trimethylsiloxy)silane,
and mixtures thereof.

Examples of at least one additional monomer may be, for example, acrylic acid, methacrylic acid, trifluoroethyl methacrylate, and mixtures thereof.

According to an embodiment, the block polymer disclosed herein may be a non-silicone polymer, i.e., a polymer free of silicon atoms.

The at least one additional monomer may be generally present in an amount of less than or equal to 30% by weight, for example from 1% to 30% by weight, in another embodiment from 5% to 20% by weight, and for example from 7% to 15% by weight, relative to the total weight of the at least one first and/or second blocks.

In one embodiment, each of the first and second blocks comprises at least one monomer chosen from (meth)acrylic acid esters and (meth)acrylic acid, and mixtures thereof.

In another embodiment, each of the first and second blocks is totally derived from at least one monomer chosen from acrylic acid, (meth)acrylic acid esters, and (meth)acrylic acid, and mixtures thereof.

In one embodiment, the block polymer disclosed herein is free of styrene. "Polymer free of styrene" means that the polymer contains less than 10% by weight, relative to the total weight of the polymer, for example, less than 5% by weight, as a further example less than 2% by weight and as another example less than 1% by weight, or does not contain at all any styrene monomer including styrene and styrene derivatives such as for instance methylstyrene, chlorostyrene or chloromethylstyrene.

The block polymer disclosed herein may be obtained by free-radical solution polymerization according to the following preparation process:
  a portion of the polymerization solvent is introduced into a suitable reactor and heated until the adequate temperature for the polymerization is reached (for example between 60 and 120° C.),
  once this temperature is reached, the at least one constituent monomer of the at least one first block are introduced in the presence of some of the polymerization initiator,
  after a time T corresponding to a maximum degree of conversion of 90%, the at least one constituent monomer of the at least one second block and the rest of the initiator are introduced,
  the mixture is left to react for a time T' (ranging from 3 to 6 hours), after which the mixture is cooled to room temperature,
  the block polymer dissolved in the polymerization solvent is obtained.

The term "polymerization solvent" means a solvent or a mixture of solvents. The polymerization solvent may be chosen, for example, from ethyl acetate, butyl acetate, alcohols chosen from isopropanol and ethanol, aliphatic alkanes chosen from isododecane, and mixtures thereof. For example, the polymerization solvent is a mixture of butyl acetate and isopropanol or isododecane.

First Embodiment

According to a first embodiment, the block polymer comprises at least one first block with a Tg of greater than or equal to 40° C., as described above in a) and at least one second block with a Tg of less than or equal to 20° C., as described above in b).

For example, the at least one first block with a Tg of greater than or equal to 40° C. may be a copolymer derived from at least one monomer wherein the homopolymer prepared from at least one monomer has a glass transition temperature of greater than or equal to 40° C., for example the at least one monomer described above.

The at least one second block with a Tg of less than or equal to 20° C. may be a homopolymer derived from at least one monomer wherein the homopolymer prepared from at least one monomer has a glass transition temperature of less than or equal to 20° C., for example the at least one monomer described above.

the at least one first block with a Tg of greater than or equal to 40° C. is present in an amount ranging from 20% to 90%, for example from 30% to 80%, and as a further example from 50% to 70% by weight of the block polymer. For example, the at least one second block with a Tg of less than or equal to 20° C. is present in an amount ranging from 5% to 75%, for example from 15% to 50%, and in a further example from 25% to 45% by weight of the block polymer.

Thus, according to a first variant, the block polymer disclosed herein may comprise:
  at least one first block with a Tg of greater than or equal to 40° C., for example having a Tg ranging from 70 to 110° C., which may be a methyl methacrylate/acrylic acid copolymer,
  at least one second block with a Tg of less than or equal to 20° C., for example ranging from 0 to 20° C., which may be a methyl acrylate homopolymer, and
  at least one intermediate segment which may be a methyl methacrylate/acrylic acid/methyl acrylate copolymer.

According to a second variant, the block polymer may comprise:
  at least one first block with a Tg of greater than or equal to 40° C., for example ranging from 70 to 100° C., which may be a methyl methacrylate/acrylic acid/trifluoroethyl methacrylate copolymer,
  at least one second block with a Tg of less than or equal to 20° C., for example ranging from 0 to 20° C., which may be a methyl acrylate homopolymer, and
  at least one intermediate segment which may be a methyl methacrylate/acrylic acid/methyl acrylate/trifluoroethyl methacrylate random copolymer.

According to a third variant, the block polymer may comprise:
  at least one first block with a Tg of greater than or equal to 40° C., for example ranging from 0 to 20° C., which may be an isobornyl acrylate/isobutyl methacrylate copolymer,
  at least one second block with a Tg of less than or equal to 20° C., for example ranging from −85 to −55° C., which may be a 2-ethylhexyl acrylate homopolymer, and
  at least one intermediate segment, which may be an isobornyl acrylate/isobutyl methacrylate/2-ethylhexyl acrylate random copolymer.

According to a fourth variant, the block polymer may comprise:
  at least one first block with a Tg of greater than or equal to 40° C., for example ranging from 85 to 115° C., which may be an isobornyl acrylate/methyl methacrylate copolymer,
  at least one second block with a Tg of less than or equal to 20° C., for example ranging from −85 to −55° C., which may be a 2-ethylhexyl acrylate homopolymer, and
  at least one intermediate segment which may be an isobornyl acrylate/methyl methacrylate/2-ethylhexyl acrylate random copolymer.

According to a fifth variant, the block polymer disclosed herein may comprise:
- at least one first block with a Tg of greater than or equal to 40° C., for example ranging from 95 to 125° C., which may be an isobornyl acrylate/isobornyl methacrylate copolymer,
- at least one second block with a Tg of less than or equal to 20° C., for example ranging from −85 to −55° C., which may be a 2-ethylhexyl acrylate homopolymer, and
- at least one intermediate segment which may be an isobornyl acrylate/isobornyl methacrylate/2-ethylhexyl acrylate random copolymer.

According to a sixth variant, the block polymer may comprise:
- at least one first block with a Tg of greater than or equal to 40° C., for example ranging from 85 to 115° C., which may be an isobornyl methacrylate/isobutyl methacrylate copolymer,
- at least one second block with a Tg of less than or equal to 20° C., for example ranging from −35 to −5° C., which may be an isobutyl acrylate homopolymer, and
- at least one intermediate segment which may be an isobornyl methacrylate/isobutyl methylacrylate/isobutyl acrylate random copolymer.

According to a seventh variant, the block polymer may comprise:
- at least one first block with a Tg of greater than or equal to 40° C., for example ranging from 95 to 125° C., which may be an isobornyl acrylate/isobornyl methacrylate copolymer,
- at least one second block with a Tg of less than or equal to 20° C., for example ranging from −35 to −5° C., which may be an isobutyl acrylate homopolymer, and
- at least one intermediate segment which may be an isobornyl acrylate/isobornyl methacrylate/isobutyl acrylate random copolymer.

According to an eighth variant, the block polymer may comprise:
- at least one first block with a Tg of greater than or equal to 40° C., for example ranging from 60 to 90° C., which may be an isobornyl acrylate/isobutyl methacrylate copolymer,
- at least one second block with a Tg of less than or equal to 20° C., for example ranging from −35 to −5° C., which may be an isobutyl acrylate homopolymer, and
- at least one intermediate segment which may be an isobornyl acrylate/isobutyl methacrylate/isobutyl acrylate random copolymer.

The examples that follow illustrate, in a non-limiting manner, block polymers corresponding to the first embodiment disclosed above.

The amounts are expressed in grams.

Example 1

Preparation of a poly(methyl methacrylate)/acrylic acid/methyl acrylate)polymer 100 g of butyl acetate were introduced into a 1 liter reactor and the temperature was then raised so as to pass from room temperature (25° C.) to 90° C. in 1 hour. 180 g of methyl methacrylate, 30 g of acrylic acid, 40 g of butyl acetate, 70 g of isopropanol and 1.8 g of 2,5-bis(2-ethylhexanoylperoxy)-2,5-dimethylhexane (TRIGONOX® 141 from Akzo Nobel) were then added, at 90° C. and over 1 hour.

The mixture was maintained at 90° C. for 1 hour.

90 g of methyl acrylate, 70 g of butyl acetate, 20 g of isopropanol and 1.2 g of 2,5-bis(2-ethylhexanoylperoxy)-2,5-dimethylhexane were then introduced into the above mixture, still at 90° C. and over 1 hour.

The mixture was maintained at 90° C. for 3 hours and then diluted with 105 g of butyl acetate and 45 g of isopropanol, and the mixture was then cooled.

A solution containing 40% polymer active material in a butyl acetate/isopropanol mixture was obtained.

A block polymer comprising a poly(methyl methacrylate/acrylic acid) first block with a Tg of 100° C., a polymethyl acrylate second block with a Tg of 10° C. and an intermediate segment which was a methyl methacrylate/acrylic acid/polymethyl acrylate random polymer was obtained.

This polymer had a weight-average mass of 52 000 and a number-average mass of 18 000, i.e., a polydispersity index I of 2.89.

Example 2

Preparation of a poly(methyl methacrylate)/acrylic acid/methyl methacrylate)polymer 100 g of butyl acetate were introduced into a 1 liter reactor and the temperature was then raised so as to pass from room temperature (25° C.) to 90° C. in 1 hour. 150 g of methyl methacrylate, 30 g of acrylic acid, 30 g of methyl acrylate, 40 g of butyl acetate, 70 g of isopropanol and 1.8 g of 2,5-bis(2-ethylhexanoylperoxy)-2,5-dimethylhexane (TRIGONOX® 141 from Akzo Nobel) were then added, at 90° C. and over 1 hour.

The mixture was maintained at 90° C. for 1 hour.

90 g of methyl acrylate, 70 g of butyl acetate, 20 g of isopropanol and 1.2 g of 2,5-bis(2-ethylhexanoylperoxy)-2,5-dimethylhexane were then introduced into the above mixture, still at 90° C. and over 1 hour.

The mixture was maintained at 90° C. for 3 hours and then diluted with 105 g of butyl acetate and 45 g of isopropanol, and the mixture was then cooled.

A solution containing 40% polymer active material in a butyl acetate/isopropanol mixture was obtained.

A block polymer comprising a poly(acrylic acid/methyl methacrylate) first block with a Tg of 80° C., a polymethyl acrylate second block with a Tg of 10° C. and an intermediate segment which was an acrylic acid/methyl acrylate/polymethyl acrylate random polymer was obtained.

This block polymer had a weight-average mass of 50 000 and a number-average mass of 17 000, i.e., a polydispersity index I of 2.95.

Example 3

Preparation of a poly(acrylic acid/methyl acrylate/polymethyl acrylate/trifluoroethyl methacrylate)polymer 100 g of butyl acetate were introduced into a 1 liter reactor and the temperature was then raised so as to pass from room temperature (25° C.) to 90° C. in 1 hour. 120 g of methyl methacrylate, 30 g of acrylic acid, 60 g of trifluoroethyl methacrylate, 40 g of butyl acetate, 70 g of isopropanol and 1.8 g of 2,5-bis(2-ethyl-hexanoylperoxy)-2,5-dimethylhexane (TRIGONOX® 141 from Akzo Nobel) were then added, at 90° C. and over 1 hour.

The mixture was maintained at 90° C. for 1 hour.

90 g of methyl acrylate, 70 g of butyl acetate, 20 g of isopropanol and 1.2 g of 2,5-bis(2-ethylhexanoylperoxy)-2,5-dimethylhexane were then introduced into the above mixture, still at 90° C. and over 1 hour.

The mixture was maintained at 90° C. for 3 hours and then diluted with 105 g of butyl acetate and 45 g of isopropanol, and the mixture was then cooled.

A solution containing 40% polymer active material in a butyl acetate/isopropanol mixture was obtained.

A block polymer comprising a poly(acrylic acid/methyl methacrylate/trifluoroethyl methacrylate) first block with a Tg of 85° C., a polymethyl acrylate second block with a Tg of 10° C. and an intermediate segment which was an acrylic acid/methyl acrylate/polymethyl acrylate/trifluoroethyl methacrylate random polymer was obtained.

This block polymer had a weight-average mass of 53 000 and a number-average mass of 17 500, i.e., a polydispersity index I of 3.03.

Example 4

Preparation of a poly(isobornyl acrylate/isobutyl methacrylate/2-ethylhexyl acrylate)polymer 100 g of isododecane were introduced into a 1 liter reactor and the temperature was then increased so as to pass from room temperature (25° C.) to 90° C. over 1 hour. 120 g of isobornyl acrylate, 90 g of isobutyl methacrylate, 110 g of isododecane and 1.8 g of 2,5-bis(2-ethylhexanoylperoxy)-2,5-dimethylhexane (TRIGONOX® 141 from Akzo Nobel) were then added, at 90° C. and over 1 hour.

The mixture was maintained at 90° C. for 1 hour 30 minutes.

90 g of 2-ethylhexyl acrylate, 90 g of isododecane and 1.2 g of 2,5-bis(2-ethylhexanoylperoxy)-2,5-dimethylhexane were then introduced into the above mixture, still at 90° C. and over 30 minutes.

The mixture was maintained at 90° C. for 3 hours and was then cooled.

A solution containing 50% polymer active material in isododecane was obtained.

A block polymer comprising a poly(isobornyl acrylate/isobutyl methacrylate) first block with a Tg of 80° C., a poly-2-ethylhexyl acrylate second block with a Tg of –70° C. and an intermediate segment which was an isobornyl acrylate/isobutyl methacrylate/2-ethylhexyl acrylate random polymer was obtained.

This block polymer had a weight-average mass of 77 000 and a number-average mass of 19 000, i.e., a polydispersity index I of 4.05.

Example 5

Preparation of a poly(isobornyl acrylate/methyl methacrylate/2-ethylhexyl acrylate)polymer 100 g of isododecane were introduced into a 1 liter reactor and the temperature was then increased so as to pass from room temperature (25° C.) to 90° C. over 1 hour. 150 g of isobornyl acrylate, 60 g of methyl methacrylate, 110 g of isododecane and 1.8 g of 2,5-bis(2-ethylhexanoylperoxy)-2,5-dimethylhexane (TRIGONOX® 141 from Akzo Nobel) were then added, at 90° C. and over 1 hour.

The mixture was maintained at 90° C. for 1 hour 30 minutes.

90 g of 2-ethylhexyl acrylate, 90 g of isododecane and 1.2 g of 2,5-bis(2-ethylhexanoylperoxy)-2,5-dimethylhexane were then introduced into the above mixture, still at 90° C. and over 30 minutes.

The mixture was maintained at 90° C. for 3 hours and was then cooled.

A solution containing 50% polymer active material in isododecane was obtained.

A block polymer comprising a poly(isobornyl acrylate/methyl methacrylate) first block with a Tg of 100° C., a poly-2-ethylhexyl acrylate second block with a Tg of –70° C. and an intermediate segment which was an isobornyl acrylate/methyl methacrylate/2-ethylhexyl acrylate random polymer was obtained.

This block polymer had a weight-average mass of 76 500 and a number-average mass of 22 000, i.e., a polydispersity index I of 3.48.

Example 6

Preparation of a poly(isobornyl acrylate/methyl methacrylate/2-ethylhexyl acrylate)polymer 100 g of isododecane were introduced into a 1 liter reactor and the temperature was then increased so as to pass from room temperature (25° C.) to 90° C. over 1 hour. 90 g of isobornyl acrylate, 60 g of methyl methacrylate, 50 g of isododecane and 1.5 g of 2,5-bis(2-ethylhexanoylperoxy)-2,5-dimethylhexane (TRIGONOX® 141 from Akzo Nobel) were then added, at 90° C. and over 1 hour.

The mixture was maintained at 90° C. for 1 hour 30 minutes.

150 g of 2-ethylhexyl acrylate, 150 g of isododecane and 1.5 g of 2,5-bis(2-ethylhexanoylperoxy)-2,5-dimethylhexane were then introduced into the above mixture, still at 90° C. and over 1 hour.

The mixture was maintained at 90° C. for 3 hours and was then cooled.

A solution containing 50% polymer active material in isododecane was obtained.

A block polymer comprising a poly(isobornyl acrylate/methyl methacrylate) first block with a Tg of 100° C., a poly-2-ethylhexyl acrylate second block with a Tg of –70° C. and an intermediate segment which was an isobornyl acrylate/methyl methacrylate/2-ethylhexyl acrylate random polymer was obtained.

This block polymer had a weight-average mass of 76 500 and a number-average mass of 22 000, i.e., a polydispersity index I of 3.48.

Example 7

Preparation of a poly(isobornyl acrylate/isobornyl methacrylate/2-ethyl hexyl acrylate)polymer 100 g of isododecane were introduced into a 1 liter reactor and the temperature was then increased so as to pass from room temperature (25° C.) to 90° C. over 1 hour. 105 g of isobornyl acrylate, 105 g of isobornyl methacrylate, 110 g of isododecane and 1.8 g of 2,5-bis(2-ethylhexanoylperoxy)-2,5-dimethylhexane (TRIGONOX® 141 from Akzo Nobel) were then added, at 90° C. and over 1 hour.

The mixture was maintained at 90° C. for 1 hour 30 minutes.

90 g of 2-ethylhexyl acrylate, 90 g of isododecane and 1.2 g of 2,5-bis(2-ethylhexanoylperoxy)-2,5-dimethylhexane were then introduced into the above mixture, still at 90° C. and over 30 minutes.

The mixture was maintained at 90° C. for 3 hours and was then cooled.

A solution containing 50% polymer active material in isododecane was obtained.

A block polymer comprising a poly(isobornyl acrylate/isobornyl methacrylate) first block with a Tg of 110° C., a poly-2-ethylhexyl acrylate second block with a Tg of −70° C. and an intermediate segment which was an isobornyl acrylate/isobornyl methacrylate/2-ethylhexyl acrylate random polymer was obtained.

This block polymer had a weight-average mass of 103 900 and a number-average mass of 21 300, i.e., a polydispersity index I of 4.89.

Example 8

Preparation of a poly(isobornyl methacrylate/isobutyl methacrylate/isobutyl acrylate)polymer 100 g of isododecane were introduced into a 1 liter reactor and the temperature was then increased so as to pass from room temperature (25° C.) to 90° C. over 1 hour. 120 g of isobornyl methacrylate, 90 g of isobutyl methacrylate, 110 g of isododecane and 1.8 g of 2,5-bis(2-ethylhexanoylperoxy)-2,5-dimethylhexane (TRIGONOX® 141 from Akzo Nobel) were then added, at 90° C. and over 1 hour.

The mixture was maintained at 90° C. for 1 hour 30 minutes.

90 g of isobutyl acrylate, 90 g of isododecane and 1.2 g of 2,5-bis(2-ethylhexanoylperoxy)-2,5-dimethylhexane were then introduced into the above mixture, still at 90° C. and over 30 minutes.

The mixture was maintained at 90° C. for 3 hours and was then cooled.

A solution containing 50% polymer active material in isododecane was obtained.

A block polymer comprising a poly(isobornyl methacrylate/isobutyl methacrylate) first block with a Tg of 95° C., a polyisobutyl acrylate second block with a Tg of −20° C. and an intermediate segment which was an isobornyl methacrylate/isobutyl methacrylate/isobutyl acrylate random polymer was obtained.

This block polymer had a weight-average mass of 100 700 and a number-average mass of 20 800, i.e., a polydispersity index I of 4.85.

Example 9

Preparation of a poly(isobornyl acrylate/isobornyl methacrylate/isobutyl acrylate)polymer 100 g of isododecane were introduced into a 1 liter reactor and the temperature was then increased so as to pass from room temperature (25° C.) to 90° C. over 1 hour. 105 g of isobornyl acrylate, 105 g of isobornyl methacrylate, 110 g of isododecane and 1.8 g of 2,5-bis(2-ethylhexanoylperoxy)-2,5-dimethylhexane (TRIGONOX® 141 from Akzo Nobel) were then added, at 90° C. and over 1 hour.

The mixture was maintained at 90° C. for 1 hour 30 minutes.

90 g of isobutyl acrylate, 90 g of isododecane and 1.2 g of 2,5-bis(2-ethylhexanoylperoxy)-2,5-dimethylhexane were then introduced into the above mixture, still at 90° C. and over 30 minutes.

The mixture was maintained at 90° C. for 3 hours and was then cooled.

A solution containing 50% polymer active material in isododecane was obtained.

A block polymer comprising a poly(isobornyl acrylate/isobornyl methacrylate) first block with a Tg of 110° C., a polyisobutyl acrylate second block with a Tg of −20° C. and an intermediate segment which was an isobornyl acrylate/isobornyl methacrylate/isobutyl acrylate random polymer was obtained.

This block polymer had a weight-average mass of 151 000 and a number-average mass of 41 200, i.e. a polydispersity index I of 3.66.

Example 10

Preparation of a poly(isobornyl acrylate/isobutyl methacrylate/isobutyl acrylate)polymer 100 g of isododecane were introduced into a 1 liter reactor and the temperature was then increased so as to pass from room temperature (25° C.) to 90° C. over 1 hour. 120 g of isobornyl acrylate, 90 g of isobutyl methacrylate, 110 g of isododecane and 1.8 g of 2,5-bis(2-ethylhexanoylperoxy)-2,5-dimethylhexane (TRIGONOX® 141 from Akzo Nobel) were then added, at 90° C. and over 1 hour.

The mixture was maintained at 90° C. for 1 hour 30 minutes.

90 g of isobutyl acrylate, 90 g of isododecane and 1.2 g of 2,5-bis(2-ethylhexanoylperoxy)-2,5-dimethylhexane were then introduced into the above mixture, still at 90° C. and over 30 minutes.

The mixture was maintained at 90° C. for 3 hours and was then cooled.

A solution containing 50% polymer active material in isododecane was obtained.

A block polymer comprising a poly(isobornyl acrylate/isobutyl methacrylate) first block with a Tg of 75° C., a polyisobutyl acrylate second block with a Tg of −20° C. and an intermediate segment which was an isobornyl acrylate/isobutyl methacrylate/isobutyl acrylate random polymer was obtained.

This block polymer had a weight average mass of 144 200 and a number-average mass of 49 300, i.e. a polydispersity index I of 2.93.

Second Embodiment

According to a second embodiment, the block polymer disclosed herein comprises at least one first block having a glass transition temperature (Tg) of between 20 and 40° C., in accordance with the blocks described in c) and at least one second block having a glass transition temperature of less than or equal to 20° C., as described above in b) or a glass transition temperature of greater than or equal to 40° C., as described in a) above.

The at least one first block with a Tg of between 20 and 40° C. ranges is present in an amount from 10% to 85% by weight of the polymer, for example from 30% to 80%, and as a further example from 50% to 70%.

When the at least one second block is a block with a Tg of greater than or equal to 40° C., it may be, for example present in an amount ranging from 10% to 85% by weight, for example from 20% to 70%, and as a further example from 30% to 70% by weight of the block polymer.

When the at least one second block is a block with a Tg of less than or equal to 20° C., it may be, for example, present in an amount ranging from 10% to 85% by weight, for example from 20% to 70%, and as a further example from 20% to 50% by weight of the block polymer.

For example, the at least one first block with a Tg of between 20 and 40° C. may be a copolymer derived from at least one monomer wherein the corresponding homopolymer has a Tg of greater than or equal to 40° C., and from at least one monomer wherein the corresponding homopolymer has a Tg of less than or equal to 20° C.

The at least one second block with a Tg of less than or equal to 20° C. or with a Tg of greater than or equal to 40° C. may be a homopolymer.

Thus, according to a first variant of this second embodiment, the block polymer may comprise:
- at least one first block with a Tg of between 20 and 40° C., for example with a Tg of 25 to 39° C., which may be a copolymer comprising at least one methyl acrylate monomer, at least one methyl methacrylate monomer, and at least one acrylic acid monomer,
- at least one second block with a Tg of greater than or equal to 40° C., for example ranging from 85 to 125° C., which may be a homopolymer composed of methyl methacrylate monomers, and
- at least one intermediate segment comprising at least one methyl acrylate, methyl methacrylate monomer, and
- at least one intermediate segment comprising methyl methacrylate, at least one acrylic acid monomer, and at least one methyl acrylate monomer.

According to a second variant of this second embodiment, the block polymer may comprise:
- at least one first block with a Tg of between 20 and 40° C., for example with a Tg of 21 to 39° C., which may be a copolymer comprising isobornyl acrylate/isobutyl methacrylate/2-ethylhexyl acrylate,
- at least one second block with a Tg of less than or equal to 20° C., for example ranging from −65 to −35° C., which may be a methyl methacrylate homopolymer, and
- at least one intermediate segment which may be an isobornyl acrylate/isobutyl methacrylate/2-ethylhexyl acrylate random copolymer.

According to a third variant of this second embodiment, the block polymer may comprise:
- at least one first block with a Tg of between 20 and 40° C., for example with a Tg from 21 to 39° C., which may be an isobornyl acrylate/methyl acrylate/acrylic acid copolymer,
- at least one second block with a Tg of greater than or equal to 40° C., for example ranging from 85 to 115° C., which may be an isobornyl acrylate homopolymer, and
- at least one intermediate segment which may be an isobornyl acrylate/methyl acrylate/acrylic acid random copolymer.

As a non-limiting illustration, the block polymers corresponding to this second embodiment may be prepared as follows.

Example 11

Preparation of a poly(butyl methacrylate/butyl acrylate)polymer 100 g of butyl acetate were introduced into a 1 liter reactor and the temperature was then increased so as to pass from room temperature (25° C.) to 90° C. over 1 hour. 210 g of butyl methacrylate, 110 g of butyl acetate and 1.8 g of 2,5-bis(2-ethylhexanoylperoxy)-2,5-dimethylhexane (TRIGONOX® 141 from Akzo Nobel) were then added, at 90° C. and over 1 hour.

The mixture was maintained at 90° C. for 1 hour 30 minutes.

90 g of butyl acrylate, 90 g of isopropanol and 1.2 g of 2,5-bis(2-ethylhexanoylperoxy)-2,5-dimethylhexane were then introduced into the above mixture, still at 90° C. and over 1 hour.

The mixture was maintained at 90° C. for 3 hours and was then diluted with 105 g of butyl acetate and 45 g of isopropanol, and then cooled.

A solution containing 40% of polymer active material in a butyl acetate/isopropanol mixture was obtained.

A block polymer comprising a polybutyl methacrylate first block with a Tg of 25° C., a polybutyl acrylate second block with a Tg of −50° C. and an intermediate segment which was a butyl methacrylate/butyl acrylate random polymer was obtained.

This block polymer had a weight-average mass of 57 560 and a number-average mass of 19 025, i.e. a polydispersity index I of 3.03.

Example 12

Preparation of a poly(methyl methacrylate/methyl acrylate/acrylic acid)polymer 100 g of butyl acetate were introduced into a 1 liter reactor and the temperature was then raised so as to pass from room temperature (25° C.) to 90° C. over 1 hour. 50.4 g of methyl methacrylate, 21 g of acrylic acid, 138.6 g of methyl acrylate, 40 g of butyl acetate, 70 g of isopropanol and 1.8 g of 2,5-bis (2-ethylhexanoylperoxy)-2,5-dimethylhexane (TRIGONOX® 141 from Akzo Nobel) were then added, at 90° C. and over 1 hour.

The mixture was maintained at 90° C. for 1 hour.

90 g of methyl methacrylate, 70 g of butyl acetate, 20 g of isopropanol and 1.2 g of 2,5-bis(2-ethylhexanoylperoxy)-2,5-dimethylhexane were then introduced into the above mixture, still at 90° C. and over 1 hour.

The mixture was maintained at 90° C. for 3 hours and then diluted with 105 g of butyl acetate and 45 g of isopropanol, and cooled.

A solution containing 40% polymer active material in a butyl acetate/isopropanol mixture was obtained.

The block polymer obtained comprises a poly(methyl acrylate/methyl methacrylate/acrylic acid) first block with a Tg of 35° C., a poly(methyl methacrylate) second block with a Tg of 100° C. and an intermediate segment which was a methyl methacrylate/acrylic acid/polymethyl acrylate random polymer.

Example 13

Preparation of a poly(isobornyl acrylate/isobutyl methacrylate/2-ethylhexyl acrylate)polymer 100 g of isododecane were introduced into a 1 liter reactor and the temperature was then increased so as to pass from room temperature (25° C.) to 90° C. over 1 hour. 105 g of isobornyl acrylate, 50.4 g of isobutyl methacrylate, 54.6 g of 2-ethylhexyl acrylate, 110 g of isododecane and 1.8 g of 2,5-bis(2-ethylhexanoyl-peroxy)-2,5-dimethylhexane (TRIGONOX® 141 from Akzo Nobel) were then added, at 90° C. and over 1 hour. This mixture was maintained at 90° C. for 1 hour 30 minutes.

90 g of 2-ethylhexyl acrylate, 90 g of isododecane and 1.2 g of 2,5-bis(2-ethylhexanoylperoxy)-2,5-dimethylhexane were then introduced into the above mixture, still at 90° C. and over 1 hour.

The mixture was maintained at 90° C. for 3 hours and was then diluted and cooled.

A solution containing 50% polymer active material in isododecane was obtained.

The block polymer obtained comprises a poly(isobornyl acrylate/isobutyl methacrylate/2-ethylhexyl acrylate) first block with a Tg of 35° C., a poly(2-ethylhexyl acrylate) second block with a Tg of –50° C. and an intermediate segment which was an isobornyl acrylate/isobutyl methacrylate/2-ethylhexyl acrylate random polymer.

Example 14

Preparation of a poly(isobornyl acrylate/isobutyl methacrylate/2-ethylhexyl acrylate)polymer 100 g of isododecane were introduced into a 1 liter reactor and the temperature was then increased so as to pass from room temperature (25° C.) to 90° C. over 1 hour. 54 g of isobornyl acrylate, 75.6 g of isobutyl methacrylate, 50.4 g of 2-ethylhexyl acrylate, 110 g of isododecane and 1.8 g of 2,5-bis(2-ethylhexanoyl-peroxy)-2,5-dimethylhexane (TRIGONOX® 141 from Akzo Nobel) were then added, at 90° C. and over 1 hour. The mixture was maintained at 90° C. for 1 hour 30 minutes.

120 g of 2-ethylhexyl acrylate, 90 g of isododecane and 1.2 g of 2,5-bis(2-ethylhexanoylperoxy)-2,5-dimethyl hexane were then introduced into the above mixture, still at 90° C. and over 1 hour.

The mixture was maintained at 90° C. for 3 hours and was then diluted and cooled.

A solution containing 50% polymer active material in isododecane was obtained.

A block polymer comprising a poly(isobornyl acrylate/isobutyl methacrylate/2-ethylhexyl acrylate) first block with a Tg of 25° C., a poly(2-ethylhexyl acrylate) second block with a Tg of –50° C. and an intermediate segment which was an isobornyl acrylate/isobutyl methacrylate/2-ethylhexyl acrylate random polymer was obtained.

Example 15

Preparation of a poly(isobornyl acrylate/acrylic acid/methyl acrylate)polymer 100 g of isododecane were introduced into a 1 liter reactor and the temperature was then increased so as to pass from room temperature (25° C.) to 90° C. over 1 hour. 210 g of isobornyl acrylate, 110 g of isododecane and 1.8 g of 2,5-bis(2-ethylhexanoylperoxy)-2,5-dimethylhexane (TRIGONOX® 141 from Akzo Nobel) were then added, at 90° C. and over 1 hour.

The mixture was maintained at 90° C. for 1 hour 30 minutes.

18 g of isobornyl acrylate, 71.1 g of methyl acrylate, 0.9 g of acrylic acid, 90 g of isododecane and 1.2 g of 2,5-bis(2-ethylhexanoylperoxy)-2,5-dimethylhexane were then introduced into the above mixture, still at 90° C. and over 1 hour.

The mixture was maintained at 90° C. for 3 hours and was then diluted and cooled.

A solution containing 50% polymer active material in isododecane was obtained.

A polymer comprising a poly(isobornyl acrylate/methyl acrylate/acrylic acid) first block with a Tg of 25° C., a polyisobornyl acrylate second block with a Tg of 100° C. and an intermediate segment which was an (isobornyl acrylate/methyl acrylate/acrylic acid) random polymer was obtained.

The following polymer was prepared:

Example 16

Preparation of a poly(methyl methacrylate/methyl acrylate/acrylic acid)polymer 210 g of ethyl acetate were introduced into a 1 liter reactor and the temperature was then increased so as to pass from room temperature (25° C.) to 78° C. over 1 hour. 54 g of methyl methacrylate, 21 g of acrylic acid, 135 g of methyl acrylate and 1.8 g of 2,5-bis(2-ethylhexanoylperoxy)-2,5-dimethylhexane (TRIGONOX® 141 from Akzo Nobel) were then added, at 78° C. and over 1 hour.

The mixture was maintained at 90° C. for 1 hour.

90 g of methyl methacrylate, 90 g of ethyl acetate and 1.2 g of 2,5-bis(2-ethylhexanoylperoxy)-2,5-dimethylhexane were then introduced into the above mixture, still at 78° C. and over 1 hour.

The mixture was maintained at 78° C. for 3 hours and was then diluted with 150 g of ethyl acetate and cooled.

A solution containing 40% polymer active material in ethyl acetate was obtained.

The block polymer obtained comprises a poly(methyl acrylate/methyl methacrylate/acrylic acid) first block with a Tg of 35° C., a poly(methyl methacrylate) second block with a Tg of 100° C. and an intermediate segment which was a methyl methacrylate/acrylic acid/polymethyl acrylate random polymer.

This block polymer had a weight-average mass of 141 000 and a number-average mass of 50 000, i.e. a polydispersity index I of 2.82.

Disclosed herein are also cosmetic compositions comprising at least one block polymer of specific structure as described above.

Generally, these compositions contain from 0.1% to 60% by weight of active material (or solids) of the block polymer disclosed herein, for example from 0.5% to 50% by weight, and as a further example from 1% to 40% by weight.

These cosmetic compositions comprise, besides the block polymers, a physiologically acceptable medium, i.e., a medium that is compatible with keratin materials, for example the skin, the hair, the eyelashes, the eyebrows, and the nails.

The physiologically acceptable medium generally comprises a physiologically acceptable suitable solvent.

The composition may thus comprise a hydrophilic medium comprising water or a mixture of water and hydrophilic organic solvent(s), for example alcohols and for example linear and branched lower monoalcohols containing from 2 to 5 carbon atoms, for example ethanol, isopropanol, or n-propanol, and polyols, for example glycerol, diglycerol, propylene glycol, sorbitol or pentylene glycol, and polyethylene glycols, or hydrophilic $C_2$ ethers and $C_2$-$C_4$ aldehydes.

The water or the mixture of water and hydrophilic organic solvents may be present in the composition in an amount ranging from 0.1% to 99% by weight, and for example from 10% to 80% by weight relative to the total weight of the composition.

The composition may comprise, besides the block polymer described above, at least one additional polymer such as a film-forming polymer. As defined herein, the term "film-forming polymer" means a polymer that may be capable, by itself or in the presence of an auxiliary film-forming agent, of forming a continuous film that adheres to a support, for example to keratin materials.

Among the film-forming polymers that may be used in the composition disclosed herein, mention may be made of synthetic polymers, of free-radical type or of polycondensate type, and polymers of natural origin, and mixtures thereof. Film-forming polymers that may be mentioned, for example, include acrylic polymers, polyurethanes, polyesters, polyamides, polyureas and cellulose-based polymers, for example nitrocellulose.

The composition may also comprise a fatty phase comprising fatty substances that are liquid at room temperature (in general 25° C.) and/or of fatty substances that are solid at room temperature, chosen from waxes, pasty fatty substances, gums, and mixtures thereof. These fatty substances may be of animal, plant, mineral or synthetic origin. This fatty phase may also contain lipophilic organic solvents.

As fatty substances that are liquid at room temperature, often referred to as oils, which may be used herein, mention may be made of: hydrocarbon-based oils of animal origin for example perhydrosqualene; hydrocarbon-based plant oils for example liquid triglycerides of fatty acids of 4 to 10 carbon atoms, for example heptanoic or octanoic acid triglycerides, or alternatively sunflower oil, maize oil, soybean oil, grapeseed oil, sesame seed oil, apricot oil, macadamia oil, castor oil, avocado oil, caprylic/capric acid triglycerides, jojoba oil, karite butter, linear or branched hydrocarbons of mineral or synthetic origin, chosen from liquid paraffin and derivatives thereof, petroleum jelly, polydecenes, hydrogenated polyisobutene for example parleam; synthetic esters and ethers, for example of fatty acids, for example purcellin oil, isopropyl myristate, 2-ethylhexyl palmitate, 2-octyldodecyl stearate, 2-octyldodecyl erucate, isostearyl isostearate; hydroxylated esters, for example isostearyl lactate, octyl hydroxystearate, octyldodecyl hydroxystearate, diisostearyl malate, triisocetyl citrate, and fatty alcohol heptanoates, octanoates and decanoates; polyol esters, for example propylene glycol dioctanoate, neopentyl glycol diheptanoate and diethylene glycol diisononanoate; and pentaerythritol esters; fatty alcohols containing from 12 to 26 carbon atoms, for example octyldodecanol, 2-butyloctanol, 2-hexyldecanol, 2-undecylpentadecanol and oleyl alcohol; partially hydrocarbon-based fluoro oils and/or fluorosilicone oils; silicone oils, chosen from volatile and non-volatile, linear and cyclic polymethylsiloxanes (PDMSs), which are liquid or pasty at room temperature, for example cyclomethicones, dimethicones, optionally comprising a phenyl group, for example phenyl trimethicones, phenyltrimethylsiloxydiphenylsiloxanes, diphenylmethyldimethyltrisiloxanes, diphenyl dimethicones, phenyl dimethicones and polymethylphenylsiloxanes; and mixtures thereof.

These oils may be present in an amount ranging from 0.01% to 90% and for example from 0.1% to 85% by weight relative to the total weight of the composition.

A "pasty fatty substance" is a viscous product comprising a liquid fraction and a solid fraction. As defined herein, the term "pasty fatty substance" is understood to mean fatty substances having a melting point ranging from 20° C. to 55° C., such as from 25° C. to 45° C., and/or a viscosity at 40° C. ranging from 0.1 to 40 Pa·s (1 to 400 poises), such as from 0.5 to 25 Pa·s, measured with a Contraves TV or Rhéomat 80 equipped with a rotor rotating at 60 Hz. The person skilled in the art can choose, from the MSr3 and MSr4 rotors, on the basis of his general knowledge, the rotor which makes it possible to measure the viscosity, so as to be able to carry out the measurement of the pasty compound tested.

The melting point values of the pasty fatty substances correspond, as disclosed herein, to the melting peak measured by the "Dynamic Scanning Colorimetry" method with a rising temperature of 5 or 10° C./min.

The composition disclosed herein may contain at least one pasty fatty substance. For example, the at least one pasty fatty substance may be chosen from hydrocarbonaceous compounds (mainly comprising carbon and hydrogen atoms and optionally ester groups), optionally of polymer type; they can also be chosen from silicone and/or fluorinated compounds; they can also be provided in the form of a mixture of hydrocarbonaceous and/or silicone and/or fluorinated compounds. In the case of a mixture of various pasty fatty substances, predominantly hydrocarbonaceous pasty compounds may be used.

In one embodiment, the at least one pasty fatty compound is chosen from lanolins and lanolin derivatives, such as acetylated lanolins or oxypropylenated lanolins or isopropyl lanolate, having a viscosity of 18 to 21 Pa·s, such as 19 to 20.5 Pa·s, and/or a melting point of 30 to 55° C., and their mixtures. The at least one pasty fatty substance may also be chosen from esters of fatty acids or of fatty alcohols, such as those having 20 to 65 carbon atoms (melting point of the order of 20 to 35° C. and/or viscosity at 40° C. ranging from 0.1 to 40 Pa·s), such as tri-isostearyl or cetyl citrate; arachidyl propionate; poly(vinyl laurate); cholesterol esters, such as triglycerides of vegetable origin, for example hydrogenated vegetable oils, viscous polyesters, such as poly(12-hydroxystearic acid), and their mixtures. For example, the at least one pasty fatty substance, as a triglyceride of vegetable origin, may be chosen from derivatives of hydrogenated castor oil, such as "Thixinr" from Rheox.

Mention may also be made of silicone pasty fatty substances, such as polydimethylsiloxanes (PDMSs) having pendent chains of the alkyl or alkoxy type having from 8 to 24 carbon atoms and a melting point of 20-55° C., such as stearyl dimethicones, for example those sold by Dow Corning under the trade names of DC2503 and D 25514, and their mixtures.

The at least one pasty fatty substance may be present in the disclosed composition in an amount ranging from 0.5 to 60% by weight with respect to the total weight of the composition, for example from 2 to 45% by weight and as a further example from 5 to 30% by weight.

The composition disclosed herein may also comprise at least one cosmetically acceptable (acceptable tolerance, toxicology and feel) organic solvent. The at least one solvent may be generally present in an amount ranging from 0 to 90%, for example from 0.1 to 90%, as a further example from 10% to 90%, and as another example from 30% to 90% by weight, relative to the total weight of the composition.

As solvents that may be used in the composition disclosed herein, mention may be made, besides the hydrophilic organic solvents mentioned above, of ketones that are liquid at room temperature chosen from methyl ethyl ketone, methyl isobutyl ketone, diisobutyl ketone, isophorone, cyclohexanone and acetone; propylene glycol ethers that are liquid at room temperature, chosen from propylene glycol monomethyl ether, propylene glycol monomethyl ether acetate, and dipropylene glycol mono-n-butyl ether; short-chain esters (containing from 3 to 8 carbon atoms in total), chosen from ethyl acetate, methyl acetate, propyl acetate, n-butyl acetate, and isopentyl acetate; ethers that are liquid at room temperature, chosen from diethyl ether, dimethyl ether, and dichlorodiethyl ether; alkanes that are liquid at room temperature, chosen from decane, heptane, dodecane, isododecane and cyclohexane; aromatic cyclic compounds that are liquid at room temperature, chosen from toluene and xylene; aldehydes that are liquid at room temperature, chosen from benzaldehyde and acetaldehyde, and mixtures thereof.

As defined herein, the term "wax" means a lipophilic compound that is solid at room temperature (25° C.), which undergoes a reversible solid/liquid change of state, and which has a melting point of greater than or equal to 30° C., which may be up to 120° C.

By bringing the wax to the liquid state (melting), it may be possible to make it miscible with the oils possibly present and to form a microscopically homogeneous mixture, but, on returning the temperature of the mixture to room temperature, recrystallization of the wax may be obtained in the oils of the mixture. The melting point of the wax may be measured using a differential scanning calorimeter (DSC), for example the calorimeter sold under the name DSC 30 by the company Mettler.

The wax may also have a hardness ranging from 0.05 MPa to 15 MPa and for example ranging from 6 MPa to 15 MPa. The hardness may be determined by measuring the compressive force, measured at 20° C. using the texturometer sold under the name TA-XT2i by the company Rheo, equipped with a stainless-steel cylinder 2 mm in diameter travelling at a measuring speed of 0.1 mm/second and penetrating the wax to a penetration depth of 0.3 mm.

The waxes may be hydrocarbon-based waxes, fluoro waxes and/or silicone waxes and may be of plant, mineral, animal and/or synthetic origin. For example, the waxes have a melting point of greater than 25° C. and for example greater than 45° C.

As waxes that may be used in the composition disclosed herein, mention may be made of beeswax, carnauba wax or candelilla wax, paraffin, microcrystalline waxes, ceresin or ozokerite, synthetic waxes, for instance polyethylene waxes or Fischer-Tropsch waxes, and silicone waxes, for instance alkyl or alkoxy dimethicones containing from 16 to 45 carbon atoms.

The gums useful herein are generally polydimethylsiloxanes (PDMSs) of high molecular weight or cellulose gums or polysaccharides.

The nature and amount of the solid substances depend on the desired mechanical properties and textures. As a guide, the composition may contain from 0 to 50% by weight and for example from 1% to 30% by weight of waxes relative to the total weight of the composition.

The polymer disclosed herein may be combined with at least one auxiliary film-forming agent. Such a film-forming agent may be chosen from any compound known to those skilled in the art as being capable of satisfying the desired function, and may be chosen for example from plasticizers and coalescers.

The composition disclosed herein may also comprise at least one dyestuff chosen from water-soluble dyes and pulverulent dyestuffs, for example pigments, nacres and flakes that are well known to those skilled in the art. The dyestuffs may be present in the composition in an amount ranging from 0.01% to 50% by weight and for example from 0.01% to 30% by weight relative to the total weight of the composition.

The term "pigments" should be understood as meaning white or colored, mineral or organic particles of any shape, which are insoluble in the physiological medium and which are intended to color the composition.

The term "nacres" should be understood as meaning iridescent particles of any shape, produced for example by certain mollusks in their shell, or alternatively synthesized.

The pigments may be white or colored, and mineral and/or organic. Among the mineral pigments that may be mentioned are titanium dioxide, optionally surface-treated, zirconium oxide or cerium oxide, and also zinc oxide, iron oxide (black, yellow or red) or chromium oxide, manganese violet, ultramarine blue, chromium hydrate and ferric blue, and metal powders, for instance aluminium powder or copper powder. Among the organic pigments that may be mentioned are carbon black, pigments of D & C type, and lakes based on cochineal carmine or on barium, strontium, calcium or aluminium.

Mention may also be made of pigments with an effect, chosen from particles comprising a natural or synthetic, organic or mineral substrate, for example glass, acrylic resins, polyester, polyurethane, polyethylene terephthalate, ceramics and aluminas, the substrate being uncoated or coated with metal substances, for example aluminium, gold, silver, platinum, copper or bronze, or with metal oxides, for example titanium dioxide, iron oxide or chromium oxide, and mixtures thereof.

The nacreous pigments may be chosen from white nacreous pigments chosen from mica coated with titanium or with bismuth oxychloride, colored nacreous pigments chosen from titanium mica coated with iron oxides, titanium mica coated for example with ferric blue or chromium oxide, titanium mica coated with an organic pigment of the above-mentioned type, and also nacreous pigments based on bismuth oxychloride. Interference pigments, for example liquid-crystal pigments or multilayer pigments, may also be used.

The water-soluble dyes may be, for example, beetroot juice or methylene blue.

The composition disclosed herein may also comprise at least one filler, for example in an amount ranging from 0.01% to 50% by weight and for example ranging from 0.01% to 30% by weight, relative to the total weight of the composition. The term "fillers" should be understood as meaning colorless or white, mineral or synthetic particles of any shape, which may be insoluble in the medium of the composition, irrespective of the temperature at which the composition is manufactured. The at least one filler serves for example to modify the rheology or the texture of the composition.

The at least one filler may be mineral or organic in any form, platelet-shaped, spherical or oblong, irrespective of the crystallographic form (for example leaflet, cubic, hexagonal, orthorhombic, etc.). Mention may be made of talc, mica, silica, kaolin, polyamide (NYLON®) powders (ORGASOL® from Atochem), poly-β-alanine powder and polyethylene powder, powders of polytetrafluoroethylene polymers (TEFLON®), lauroyllysine, starch, boron nitride, hollow polymer microspheres such as those of polyvinylidene chloride/acrylonitrile, for instance EXPANCEL® (Nobel Industrie) or acrylic acid copolymers (POLYTRAP® from the company Dow Corning) and silicone resin microbeads (for example TOSPEARLS® from Toshiba), elastomeric polyorganosiloxane particles, precipitated calcium carbonate, magnesium carbonate, magnesium hydrocarbonate, hydroxyapatite, hollow silica microspheres (SILICA BEADS® from Maprecos), glass or ceramic microcapsules, and metal soaps derived from organic carboxylic acids containing from 8 to 22 carbon atoms and for example from 12 to 18 carbon atoms, for example zinc, magnesium or lithium stearate, zinc laurate or magnesium myristate.

The composition disclosed herein may also contain ingredients commonly used in cosmetics, such as vitamins, thickeners, trace elements, softeners, sequestering agents, fragrances, acidifying or basifying agents, preserving agents, sunscreens, surfactants, antioxidants, agents for preventing hair loss, antidandruff agents and propellants, or mixtures thereof.

Needless to say, a person skilled in the art will take care to select this or these optional additional compound(s), and/or the amount thereof, so that the advantageous properties of the corresponding composition disclosed herein are not, or are not substantially, adversely affected by the envisaged addition.

The composition disclosed herein, for example, be in the form of a suspension, a dispersion, a solution, a gel, an emulsion, for example an oil-in-water (O/W) emulsion, a water-in-oil (W/O) emulsion or a multiple emulsion (W/O/W or polyol/O/W or O/W/O emulsion), in the form of a cream, a mousse, a dispersion of vesicles, for example of ionic or nonionic lipids, a two-phase or multi-phase lotion, a spray, a powder, a paste, for example a soft paste (for example a paste with a dynamic viscosity at 25° C. of about from 0.1 to 40 Pa·s under a shear rate of 200 s$^{-1}$, after measurement for 10 minutes in cone/plate geometry). The composition may be anhydrous; for example, it may be an anhydrous paste.

A person skilled in the art may select the appropriate presentation form, and also the method for preparing it, on the basis of his general knowledge, taking into account firstly the nature of the constituents used, for example their solubility in the support, and secondly the intended application for the composition.

The composition disclosed herein may be a makeup composition, for example complexion products (foundations), makeup rouges, eyeshadows, lipcare products, concealer products, blushers, mascaras, eyeliners, eyebrow makeup products, lip pencils, eye pencils, nailcare products, for example nail varnishes, body makeup products, and hair makeup products (mascara).

When the composition disclosed herein is a complexion product, it may comprise a block polymer according to the first embodiment described above, such as a polymer comprising at least one first block having a Tg ranging from 50° C. to 100° C. and at least one second block having a Tg ranging from −100° C. to 0° C. In one embodiment, the block polymer for a complexion product is chosen among the block polymers described in the third and eighth variants of the first embodiment, as described above.

The composition disclosed herein may also be a care product for body and facial skin, for example an antisun product or a skin coloring product (for example a self-tanning product).

The composition disclosed herein may also be a haircare product, for example for holding the hairstyle or shaping the hair. The hair compositions are chosen from shampoos, hair setting gels, hair setting lotions, blow-drying lotions, fixing compositions, and styling compositions.

The examples that follow illustrate, in a non-limiting manner, the compositions comprising the polymer disclosed herein.

The amounts are expressed in grams.

Example 17

Nail Varnish

A nail varnish having the composition below was prepared:

| | |
|---|---|
| Polymer of Example 1 | 23.8 g AM |
| Butyl acetate | 24.99 g |
| Isopropanol | 10.71 g |
| Hexylene glycol | 2.5 g |
| DC Red 7 Lake | 1 g |
| Hectorite modified with stearyldimethylbenzylammonium chloride (Bentone ® 27V from Elementis) | 1.3 g |
| Ethyl acetate | qs 100 |

After application to the nails, this varnish was considered as having good staying power and impact strength properties.

Example 18

Mascara Composition

A mascara having the composition below was prepared:

| | |
|---|---|
| Beeswax | 8 g |
| Paraffin wax | 3 g |
| Carnauba wax | 6 g |
| Hectorite modified with distearyldimethylbenzylammonium chloride (Bentone ® 38V from Elementis) | 5.3 g |
| Propylene carbonate | 1.7 g |
| Filler | 1 g |
| Pigments | 5 g |
| Polymer of Example 4 | 12 g AM |
| Isododecane | qs 100 |

The staying power of the mascara film, after application to the eyelashes, was considered as being very satisfactory.

Example 19

Mascara Composition

A mascara having the composition below was prepared:

| | |
|---|---|
| Beeswax | 8 g |
| Paraffin wax | 3 g |
| Carnauba wax | 6 g |
| Hectorite modified with distearyldimethylbenzylammonium chloride (Bentone ® 38V from Elementis) | 5.3 g |
| Propylene carbonate | 1.7 g |
| Filler | 1 g |
| Pigments | 5 g |
| Polymer of Example 7 | 12 g AM |
| Isododecane | qs 100 |

The staying power of the mascara film, after application to the eyelashes, was considered as being very satisfactory.

Example 20

Lipstick in Stick Form

The lipstick composition below is prepared:

| | |
|---|---|
| Polyethylene wax | 15% |
| Polymer of Example 5 | 10% AM |
| Hydrogenated polyisobutene (Parleam from Nippon Oil Fats) | 26% |
| Isododecane | qs 100 |
| Pigments | 8.6% |

The film of composition obtained after application to the lips shows good staying power properties.

Example 21

W/O Foundation

A foundation composition comprising the compounds below is prepared:

| | | |
|---|---|---|
| Phase A | Cetyldimethicone copolyol (Abil EM 90 from the company goldschmidt) | 3 g |
| | Isostearyl diglyceryl succinate (Imwitor 780K from the company Condea) | 0.6 g |
| | Isododecane | 18.5 g |
| | Mixture of pigments (hydrophobic titanium oxides and iron oxides) | 10 g |
| | Polymer of Example 5 | 8.7 g AM |
| | Polyamide powder (Nylon-12 from Dupont) | 8 g |
| | Fragrance | 0.5 g |
| Phase B | Water | qs 100 |
| | Magnesium sulphate | 0.7 g |
| | Preserving agent (methyl paraben) | 0.2 g |
| Phase C | Water | 2 g |
| | Preserving agent (diazolinylurea) | 0.25 g |

Example 22

Nail Varnish

| | |
|---|---|
| Polymer of Example 12 | 23.8 g AM |
| Butyl acetate | 24.99 g |
| Isopropanol | 10.71 g |
| Hexylene glycol | 2.5 g |
| DC Red 7 Lake | 1 g |
| Hectorite modified with stearyldimethylbenzylammonium chloride (Bentone ® 27V from Elementis) | 1.3 g |
| Ethyl acetate | qs 100 g |

Example 23

Mascara Composition

| | |
|---|---|
| Beeswax | 8 g |
| Paraffin wax | 3 g |
| Carnauba wax | 6 g |
| Hectorite modified with distearyldimethylbenzylammonium chloride (Bentone ® 38V from Elementis) | 5.3 g |
| Propylene carbonate | 1.7 g |
| Filler | 1 g |
| Pigments | 5 g |
| Polymer of Example 14 | 12 g AM |
| Isododecane | qs 100 |

Example 24

Lipstick in Stick Form

| | |
|---|---|
| Polyethylene wax | 15% |
| Polymer of Example 13 | 10% AM |
| Hydrogenated polyisobutene (Parleam from Nippon Oil Fats) | 26% |
| Isododecane | qs 100 |
| Pigments | 8.6% |

Example 25

W/O Foundation

| | | |
|---|---|---|
| Phase A | Cetyldimethicone copolyol (Abil EM 90 from the company goldschmidt) | 3 g |
| | Isostearyl diglyceryl succinate (Imwitor 780K from the company Condea) | 0.6 g |
| | Isododecane | 18.5 g |
| | Mixture of pigments (hydrophobic titanium oxides and iron oxides) | 10 g |
| | Polymer of Example 15 | 8.7 g AM |
| | Polyamide powder (Nylon-12 from Dupont de Nemours) | 8 g |
| | Fragrance | 0.5 g |
| Phase B | Water | qs 100 |
| | Magnesium sulphate | 0.7 g |
| | Preserving agent (methyl paraben) | 0.2 g |
| Phase C | Water | 2 g |
| | Preserving agent (diazolinylurea) | 0.25 g |

Example 26

W/O Foundation

| | | |
|---|---|---|
| Phase A | Mixture of oxypropylated oxyethylated dimethylpolysiloxane and of cyclodimethylpentasiloxane (85/15) (Abil EM 97 from the company goldschmidt) | 1.8 g |
| | Isostearyl diglyceryl succinate (Imwitor 780K from the company Condea) | 0.6 g |
| | Cylcopentadimethylsiloxane | 6 g |
| | Isododecane qsp | 100 g |
| | Mixture of pigments (hydrophobic titanium oxides and iron oxides) | 10 g |
| | Polymer of Example 4 | 2.1 g AM |
| | Polyamide powder (Nylon-12 from Dupont) | 8 g |
| Phase B | Water | 41.4 g |
| | Magnesium sulphate | 0.7 g |
| | Preserving agent | 0.3 g |

Example 27

W/O Foundation

| | | |
|---|---|---|
| Phase A | Mixture of oxypropylated oxyethylated dimethylpolysiloxane and of cyclodimethylpentasiloxane (85/15) (Abil EM 97 from the company Goldschmidt) | 1.8 g |
| | Isostearyl diglyceryl succinate (Imwitor 780K from the company Condea) | 0.6 g |
| | Cylcopentadimethylsiloxane | 6 g |
| | Isododecane qsp | 100 g |
| | Mixture of pigments (hydrophobic titanium oxides and iron oxides) | 10 g |
| | Polymer of Example 10 | 2.1 g AM |
| | Polyamide powder (Nylon-12 from Dupont) | 8 g |
| Phase B | Water | 41.4 g |
| | Magnesium sulphate | 0.7 g |
| | Preserving agent | 0.3 g |

What is claimed is:

1. A process for preparing a block polymer comprising at least one first block and at least one second block that are incompatible with each other and that have different glass transition temperatures (Tg), wherein the block polymer is not an elastomer, wherein the at least one first block has a Tg greater than or equal to 40° C. and is present in an amount ranging from 50% to 90% by weight of the block polymer, wherein the at least one second block has a Tg less than 20° C. and is present in an amount ranging from 5% to 45% by weight of the block polymer, wherein the at least one first and second blocks are linked together via an intermediate segment comprising at least one constituent monomer of the at least one first block and at least one constituent monomer of the at least one second block, wherein each of the at least one first and second blocks comprises at least one monomer chosen from acrylic acid, acrylic acid esters, methacrylic acid, and methacrylic acid esters, wherein said intermediate block is a random copolymer block, and wherein the block polymer has a polydispersity index I ranging from 2.8 to 6, the process comprising:

introducing a portion of polymerization solvent into a suitable reactor and heating until an adequate temperature for polymerization is reached, once the polymerization temperature is reached, introducing the constituent monomers of the first block in the presence of an polymerization initiator, after a time T corresponding to a maximum degree of conversion of 90%, introducing the constituent monomers of the second block and the rest of the polymerization solvent, leaving the mixture to react for a time T', then cooling the mixture to room temperature to obtain the polymer dissolved in the polymerization solvent.

2. The process according to claim 1, wherein the polymerization temperature ranges from 60 to 120° C.

3. A cosmetic composition comprising at least one block polymer comprising at least one first block and at least one second block that are incompatible with each other and that have different glass transition temperatures (Tg), wherein the block polymer is not an elastomer, wherein the at least one first block has a Tg greater than or equal to 40° C. and is present in an amount ranging from 50% to 90% by weight of the block polymer, wherein the at least one second block has a Tg less than 20° C. and is present in an amount ranging from 5% to 45% by weight of the block polymer, wherein the at least one first and second blocks are linked together via an intermediate segment comprising at least one constituent monomer of the at least one first block and at least one constituent monomer of the at least one second block, wherein each of the at least one first and second blocks comprises at least one monomer chosen from acrylic acid, acrylic acid esters, methacrylic acid, and methacrylic acid esters, wherein said intermediate block is a random copolymer block, and wherein the block polymer has a polydispersity index I ranging from 2.8 to 6.

4. The cosmetic composition according to claim 3, wherein said composition comprises from 0.1% to 60% by weight of polymer active material.

5. The cosmetic composition according to claim 4, wherein said composition comprises from 5% to 50% by weight of polymer active material.

6. The cosmetic composition according to claim 5, wherein said composition comprises from 10% to 40% by weight of polymer active material.

7. The cosmetic composition according to claim 3, wherein said composition comprises a physiologically acceptable medium.

8. The cosmetic composition according to claim 7, wherein said physiologically acceptable medium comprises a hydrophilic medium comprising at least one of water and mixtures of water and at least one hydrophilic organic solvent.

9. The cosmetic composition according to claim 8, wherein said at least one hydrophilic organic solvent is chosen from alcohols.

10. The cosmetic composition according to claim 9, wherein said alcohols are chosen from linear or branched lower monoalcohols comprising from 2 to 5 carbon atoms, polyols, and polyethylene glycols.

11. The cosmetic composition according to claim 10, wherein said monoalcohols are chosen from ethanol, isopropanol and n-propanol.

12. The cosmetic composition according to claim 10, wherein said polyols are chosen from glycerol, diglycerol, propylene glycol, sorbitol and pentylene glycol.

13. The cosmetic composition according to claim 3, wherein said composition further comprises a fatty phase comprising fatty substances that are liquid or solid at room temperature, and are of animal, plant, mineral or synthetic origin.

14. The cosmetic composition according to claim 3, wherein said composition further comprises at least one cosmetically acceptable organic solvent.

15. The cosmetic composition according to claim 3, wherein said composition further comprises at least one auxiliary film-forming agent chosen from plasticizers and coalescers.

16. The cosmetic composition according to claim 3, wherein said composition further comprises at least one dyestuff chosen from water-soluble dyes and pulverulent dyestuffs.

17. The cosmetic composition according to claim 16, wherein said pulverulent dyestuffs are chosen from pigments, nacres and flakes.

18. The cosmetic composition according to claim 3, wherein said composition further comprises at least one filler.

19. The cosmetic composition according to claim 3, wherein said composition further comprises at least one ingredient chosen from vitamins, thickeners, trace elements, softeners, sequestering agents, fragrances, acidifying or basifying agents, preserving agents, sunscreens, surfactants, antioxidants, agents for preventing hair loss, antidandruff agents and propellants.

20. The cosmetic composition according to claim 3, wherein said composition is in the form of a suspension, a dispersion, a solution, a gel, an emulsion, a cream, a mousse, a dispersion of vesicles, a two-phase or multi-phase lotion, a spray, a powder, or a paste.

21. The cosmetic composition according to claim 20, wherein said emulsion is chosen from an oil-in-water (O/W) emulsion, a water-in-oil (W/O) emulsion and a multiple emulsion (W/O/W or polyol/O/W or O/W/O emulsion).

22. The cosmetic composition according to claim 20, wherein said dispersion of vesicles is chosen from dispersions of ionic and of nonionic lipids.

23. The cosmetic composition according to claim 20, wherein said paste is chosen from a soft paste and an anhydrous paste.

24. A makeup or care composition for keratin materials, said composition comprising at least one block polymer comprising at least one first block and at least one second block that are incompatible with each other and that have different glass transition temperatures (Tg),
   wherein the block polymer is not an elastomer,
   wherein the at least one first block has a Tg greater than or equal to 40° C. and is present in an amount ranging from 50% to 90% by weight of the block polymer,
   wherein the at least one second block has a Tg less than 20° C. and is present in an amount ranging from 5% to 45% by weight of the block polymer,
   wherein the at least one first and second blocks are linked together via an intermediate segment comprising at least one constituent monomer of the at least one first block and at least one constituent monomer of the at least one second block,
   wherein each of the at least one first and second blocks comprises at least one monomer chosen from acrylic acid, acrylic acid esters, methacrylic acid, and methacrylic acid esters,
   wherein said intermediate block is a random copolymer block, and
   wherein the block polymer has a polydispersity index I ranging from 2.8 to 6.

25. A make-up or care composition according to claim 24, wherein said composition is chosen from a haircare product, a nail varnish, a lip makeup product, an eye makeup product, and a makeup product for the complexion.

26. A make-up or care composition according to claim 24, wherein the at least one block polymer comprises at least one first block having a glass transition temperature Tg ranging from 50° C. to 100° C. and at least one second block having a glass transition temperature Tg ranging from −100° C. to 0° C.

27. A make-up or care composition according to claim 24, wherein said at least one block polymer is chosen from:
   (i) a block polymer comprising:
      a first block with a Tg of greater than or equal to 40° C. which is an isobornyl acrylate/isobutyl methacrylate copolymer,
      a second block with a Tg of less than or equal to 20° C. which is a 2-ethylhexyl acrylate homopolymer, and
      an intermediate segment, which is an isobornyl acrylate/isobutyl methacrylate/2-ethylhexyl acrylate random copolymer, and
   (ii) a block polymer comprising:
      a first block with a Tg of greater than or equal to 40° C. which is an isobornyl acrylate/isobutyl methacrylate copolymer,
      a second block with a Tg of less than or equal to 20° C., which is an isobutyl acrylate homopolymer, and
      an intermediate segment which is an isobornyl acrylate/isobutyl methacrylate/isobutyl acrylate random copolymer.

28. A make-up or care composition according to claim 27, wherein:
   in said at least one block polymer (i):
      said first block has a Tg ranging from 0° C. to 20° C.,
      said second block has a Tg ranging from −85° C. to −55° C., and
   in said at least one block polymer (ii):
      said first block has a Tg ranging from 60° C. to 90° C., and
      said second block has a Tg ranging from −35 to −5° C.

29. A cosmetic composition according to claim 3, wherein said composition further comprises at least one additional polymer chosen from film-forming polymers.

30. A cosmetic composition according to claim 3, wherein said composition further comprises at least one fatty substance which is solid at room temperature and which is chosen from waxes, pasty fatty substances and gums.

31. A cosmetic process for making up or caring for keratin materials, comprising applying to keratin materials a cosmetic composition comprising at least one first block and at least one second block that are incompatible with each other and that have different glass transition temperatures (Tg),
   wherein the block polymer is not an elastomer,
   wherein the at least one first block has a Tg greater than or equal to 40° C. and is present in an amount ranging from 50% to 90% by weight of the block polymer,
   wherein the at least one second block has a Tg less than 20° C. and is present in an amount ranging from 5% to 45% by weight of the block polymer,
   wherein the at least one first and second blocks are linked together via an intermediate segment comprising at least one constituent monomer of the at least one first block and at least one constituent monomer of the at least one second block,
   wherein each of the at least one first and second blocks comprises at least one monomer chosen from acrylic acid, acrylic acid esters, methacrylic acid, and methacrylic acid esters,
   wherein said intermediate block is a random copolymer block, and
   wherein the block polymer has a polydispersity index I ranging from 2.8 to 6.

32. A process for improving the staying power of a cosmetic composition on keratin materials, comprising applying to keratin materials a cosmetic composition comprising at least one first block and at least one second block that are incompatible with each other and that have different glass transition temperatures (Tg),
   wherein the block polymer is not an elastomer,
   wherein the at least one first block has a Tg greater than or equal to 40° C. and is present in an amount ranging from 50% to 90% by weight of the block polymer,
   wherein the at least one second block has a Tg less than 20° C. and is present in an amount ranging from 5% to 45% by weight of the block polymer,
   wherein the at least one first and second blocks are linked together via an intermediate segment comprising at least one constituent monomer of the at least one first block and at least one constituent monomer of the at least one second block,
   wherein each of the at least one first and second blocks comprises at least one monomer chosen from acrylic acid, acrylic acid esters, methacrylic acid, and methacrylic acid esters,
   wherein said intermediate block is a random copolymer block, and
   wherein the block polymer has a polydispersity index I ranging from 2.8 to 6.

* * * * *

UNITED STATES PATENT AND TRADEMARK OFFICE
CERTIFICATE OF CORRECTION

PATENT NO. : 7,932,324 B2  Page 1 of 1
APPLICATION NO. : 11/859015
DATED : April 26, 2011
INVENTOR(S) : Bertrand Lion et al.

It is certified that error appears in the above-identified patent and that said Letters Patent is hereby corrected as shown below:

In column 1, line 6, after "filed Sep. 26, 2003,", insert --now U.S. Pat. No. 7,803,877,--.

In column 1, line 8, delete "now U.S. Pat. No. 7,803,877".

In claim 1, column 29, line 33, "an polymerization" should read --a polymerization--.

Signed and Sealed this
Nineteenth Day of July, 2011

David J. Kappos
*Director of the United States Patent and Trademark Office*